(12) United States Patent
Nair

(10) Patent No.: US 9,592,027 B2
(45) Date of Patent: Mar. 14, 2017

(54) SYSTEM AND METHOD OF ADVENTITIAL TISSUE CHARACTERIZATION

(71) Applicant: Volcano Corporation, San Diego, CA (US)

(72) Inventor: Anuja Nair, Bedford, MA (US)

(73) Assignee: Volcano Corporation, San Diego, CA (US)

( * ) Notice: Subject to any disclaimer, the term of this patent is extended or adjusted under 35 U.S.C. 154(b) by 1 day.

(21) Appl. No.: 14/212,451

(22) Filed: Mar. 14, 2014

(65) Prior Publication Data

US 2014/0270430 A1    Sep. 18, 2014

Related U.S. Application Data

(60) Provisional application No. 61/784,570, filed on Mar. 14, 2013.

(51) Int. Cl.
*A61B 8/08*  (2006.01)
*A61B 8/12*  (2006.01)
*A61B 8/00*  (2006.01)

(52) U.S. Cl.
CPC ............ *A61B 8/085* (2013.01); *A61B 8/0891* (2013.01); *A61B 8/12* (2013.01); *A61B 8/445* (2013.01); *A61B 8/463* (2013.01); *A61B 8/5215* (2013.01)

(58) Field of Classification Search
None
See application file for complete search history.

(56) References Cited

U.S. PATENT DOCUMENTS

| 5,197,470 | A  | * | 3/1993  | Helfer et al. ................ 600/342 |
| 5,749,914 | A  | * | 5/1998  | Janssen .............. A61B 18/1206 607/116 |
| 6,264,609 | B1 | * | 7/2001  | Herrington et al. .......... 600/443 |
| 6,669,686 | B1 | * | 12/2003 | Singh ..................... A61B 18/20 606/12 |
| 7,463,759 | B2 | * | 12/2008 | Klingensmith et al. ...... 382/128 |
| 7,955,265 | B2 | * | 6/2011  | Burla et al. .................. 600/458 |
| 8,131,032 | B2 | * | 3/2012  | Demi et al. .................. 382/128 |
| 2002/0086347 | A1 | * | 7/2002  | Johnson ............. A61B 5/02007 435/40.5 |
| 2002/0111618 | A1 | * | 8/2002  | Stewart ............. A61B 18/1492 606/41 |
| 2002/0193336 | A1 | * | 12/2002 | Elkins et al. .................... 514/44 |
| 2003/0088195 | A1 | * | 5/2003  | Vardi et al. .................... 600/585 |

(Continued)

OTHER PUBLICATIONS

Sanada, Jun-Ichiro, Osamu Matsui, Jun Yoshikawa, and Toshihiko Matsuoka. "An experimental study of endovascular stenting with special reference to the effects on the aortic vasa vasorum." Cardiovascular and interventional radiology 21, No. 1 (1998): 45-49.*

(Continued)

*Primary Examiner* — Sumati Lefkowitz
*Assistant Examiner* — Carol Wang

(57) ABSTRACT

Disclosed herein is a system and method for characterizing adventitial tissue. In one aspect, a system and method is disclosed that characterizes tissue types within the adventitial tissue including nerve bundles and blood vessels. In a further aspect, the adventitia is imaged and characterized to provide guidance for crossing lesions within an occluded vessel.

35 Claims, 14 Drawing Sheets

(56) References Cited

U.S. PATENT DOCUMENTS

| | | | |
|---|---|---|---|
| 2004/0116808 A1* | 6/2004 | Fritz | A61B 5/02007 600/437 |
| 2004/0147920 A1* | 7/2004 | Keidar | A61B 5/06 606/34 |
| 2005/0119555 A1* | 6/2005 | Fritz et al. | 600/410 |
| 2005/0171478 A1* | 8/2005 | Selmon et al. | 604/164.01 |
| 2006/0241577 A1* | 10/2006 | Balbierz | A61B 18/1206 606/32 |
| 2007/0038061 A1* | 2/2007 | Huennekens et al. | 600/407 |
| 2008/0138288 A1* | 6/2008 | Lanza et al. | 424/9.2 |
| 2008/0279476 A1* | 11/2008 | Rongen et al. | 382/284 |
| 2009/0196480 A1* | 8/2009 | Nields | G06T 7/0028 382/132 |
| 2010/0081933 A1* | 4/2010 | Sverdlik | A61B 5/0048 600/439 |
| 2010/0087731 A1* | 4/2010 | Ramachandran | 600/424 |
| 2010/0185156 A1* | 7/2010 | Kanner et al. | 604/190 |
| 2011/0082374 A1* | 4/2011 | Main et al. | 600/458 |
| 2011/0257523 A1* | 10/2011 | Hastings | A61B 8/0891 600/439 |
| 2012/0029509 A1* | 2/2012 | Smith | 606/41 |
| 2012/0075638 A1* | 3/2012 | Rollins et al. | 356/479 |
| 2012/0089025 A1* | 4/2012 | Toji | A61B 8/06 600/443 |
| 2012/0150046 A1* | 6/2012 | Watson | A61B 5/0071 600/478 |
| 2013/0053792 A1* | 2/2013 | Fischell et al. | 604/275 |
| 2014/0213971 A1* | 7/2014 | Dolan | A61F 2/82 604/104 |
| 2014/0358136 A1* | 12/2014 | Kelly | A61B 18/02 606/21 |
| 2015/0265241 A1* | 9/2015 | Belt | A61B 8/0833 600/424 |

OTHER PUBLICATIONS

Stöger, J. Lauran, Marion JJ Gijbels, Saskia van der Velden, Marco Manca, Chris M. van der Loos, Erik AL Biessen, Mat JAP Daemen, Esther Lutgens, and Menno PJ de Winther. "Distribution of macrophage polarization markers in human atherosclerosis." Atherosclerosis 225, No. 2 (2012): 461-468.*

Kerwin, W. S., M. Oikawa, C. Yuan, G. P. Jarvik, and T. S. Hatsukami. "MR imaging of adventitial vasa vasorum in carotid atherosclerosis." Magnetic Resonance in Medicine 59, No. 3 (2008): 507-514.*

Futamatsu, Hideki, et al. "Characterization of plaque prolapse after drug-eluting stent implantation in diabetic patients: a three-dimensional volumetric intravascular ultrasound outcome study." Journal of the American College of Cardiology 48, No. 6 (2006): 1139-1145.*

* cited by examiner

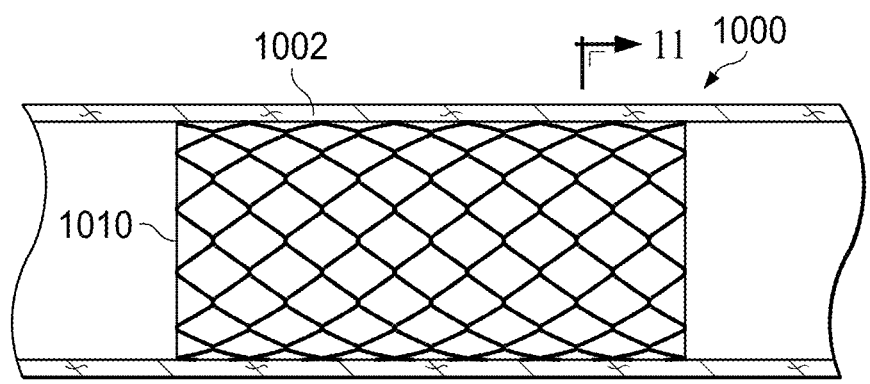
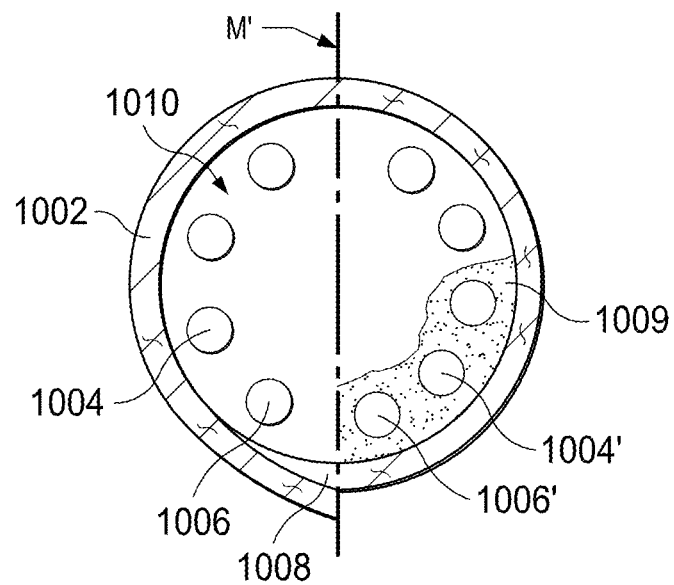

SYSTEM AND METHOD OF ADVENTITIAL TISSUE CHARACTERIZATION

CROSS-REFERENCE TO RELATED APPLICATIONS

The present application claims priority to and the benefit of U.S. Provisional Patent Application No. 61/784,570, filed Mar. 14, 2013, which is hereby incorporated by reference in its entirety.

FIELD OF THE INVENTION

The present disclosure relates generally to tissue characterization and more particularly to procedures utilization tissue characterization of the adventitial tissues.

BACKGROUND

Intravascular tissue characterization is currently performed in conjunction with the evaluation of lesions within the lumens of vessels. Such characterization generally evaluates the properties of the lesion and provides a graphic display of the tissue types for the user. Example of such tissue characterization techniques are disclosed in U.S. Pat. Nos. 7,627,156 and 7,789,834, each of which is hereby incorporated by reference in its entirety. While these systems have been sufficient at providing information concerning properties of the lesion, there remains a need to determine additional information about the vessel and surrounding supportive tissue to evaluate vessel health and determine appropriate therapies. Such additional features can also consider further aspects about prosthetic devices positioned in the vasculature.

In addition, intravascular imaging systems have been developed to identify the border between different layers within a vessel. For example, U.S. Pat. Nos. 7,463,759 and 8,233,718, each of which is incorporated herein by reference in its entirety, disclose techniques for determining the borders been various regions within the vessel. Although such techniques provide valuable information in many situations, when occlusions have disrupted vessel layer boundaries or the imaging device is not directed perpendicular to the boundaries, such boundaries may be difficult or impossible to image. Thus, there remains a need for better imaging techniques to provide additional information concerning the vessel walls.

The devices, systems, and methods disclosed herein overcome one or more of the deficiencies of the prior art.

SUMMARY

In one aspect, the present disclosure provides a system and method for performing tissue characterization of adventitial tissue of a vessel. Among other features, the adventitial tissue characterization information can assist the user in one or more of the following: evaluation of the location of nerve bundles, evaluation of tissue to be ablated, the amount of energy to utilize, the extent of the area to be ablated, damage to adjacent tissue, the direction of the tissue to be ablated, the depth of ablation, amount and direction of vasa vasorum, myocardium encroachment or positioning adjacent the adventitial tissue, and guidance across through occlusions within a vessel.

In one embodiment, the present disclosure provides a method that includes imaging a vessel including surrounding adventitial tissue and performing tissue characterization on the adventitial tissue. The results of the adventitial tissue characterization can then be displayed to a user. In one aspect, the display is a colorized display overlaid on an intravascular ultrasound image. In another aspect, the image is a three dimensional model highlighted with color to illustrate structures identified within the adventitial tissue. In one aspect, the tissue characterization includes identifying nerve bundles within the adventitial tissue. In another aspect, the imaging includes imaging the adventitia and the perivascular supportive tissue surrounding an artery and the identifying includes identifying nerve bundles within the perivascular tissue. In a further aspect, the method includes identifying myocardial muscular tissue surrounding the vessel and displaying the location to a user. In another aspect, the tissue characterization includes identifying and displaying vasa vasorum within the adventitial tissue. In another further aspect, the tissue characterization includes identifying the transition of the medial to adventitial tissue and the location of the adventitial tissue.

In another aspect of the present disclosure, a method is provided for performing a first imaging of the vessel and first tissue characterization of the adventitial tissue of the vessel, conducting a therapy on the vessel, performing a second imaging of the vessel and second tissue characterization of the adventitial tissue of the vessel, comparing the first and second tissue characterizations and displaying the differences to the user. In one aspect, additional therapy can be delivered based on the differences displayed to the user. In one embodiment, the therapy is includes an ablation therapy. In another form, the therapy includes stenting within the vessel. In still a further aspect, the time between delivery of the therapy and the second imaging is a period of at least several days, and the differences displayed illustrate changes to tissue within or around the stent and/or changes to the stent structure itself.

In still a further aspect, the present disclosure provides a system for adventitial tissue characterization. The system includes a data base of known adventitial tissue patterns, a sensor for collecting imaging data from a vessel, and a processor configured to compare the sensor imaging data to the data base of known adventitial tissue patterns and determine tissue characterizations within the adventitial tissues.

In yet a further aspect, the present disclosure provides a method for utilizing tissue characterization in image guided therapy. In one aspect, the method includes positioning an imaging device and a therapy device within the lumen of a vessel and imaging the vessel including the adventitial tissue surrounding at least a portion of the lumen. The method continues with performing tissue characterization on the adventitial tissue and displaying adventitial tissue characteristics to a use. The position of the therapy device can then be changed in response to the displayed adventitial tissue characteristics. In one aspect, the method includes defining a longitudinal direction of the therapy device and alerting to the user to the presence of adventitial tissue in the longitudinal direction of the therapy device. In still a further aspect, the therapy device is a chronic total occlusion crossing device and the changing includes changing the longitudinal direction of the device. In yet a further aspect, the therapy device is an ablation device and the changing includes changing the longitudinal or radial position of the ablation device within the vessel in response to the adventitial tissue characteristics.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
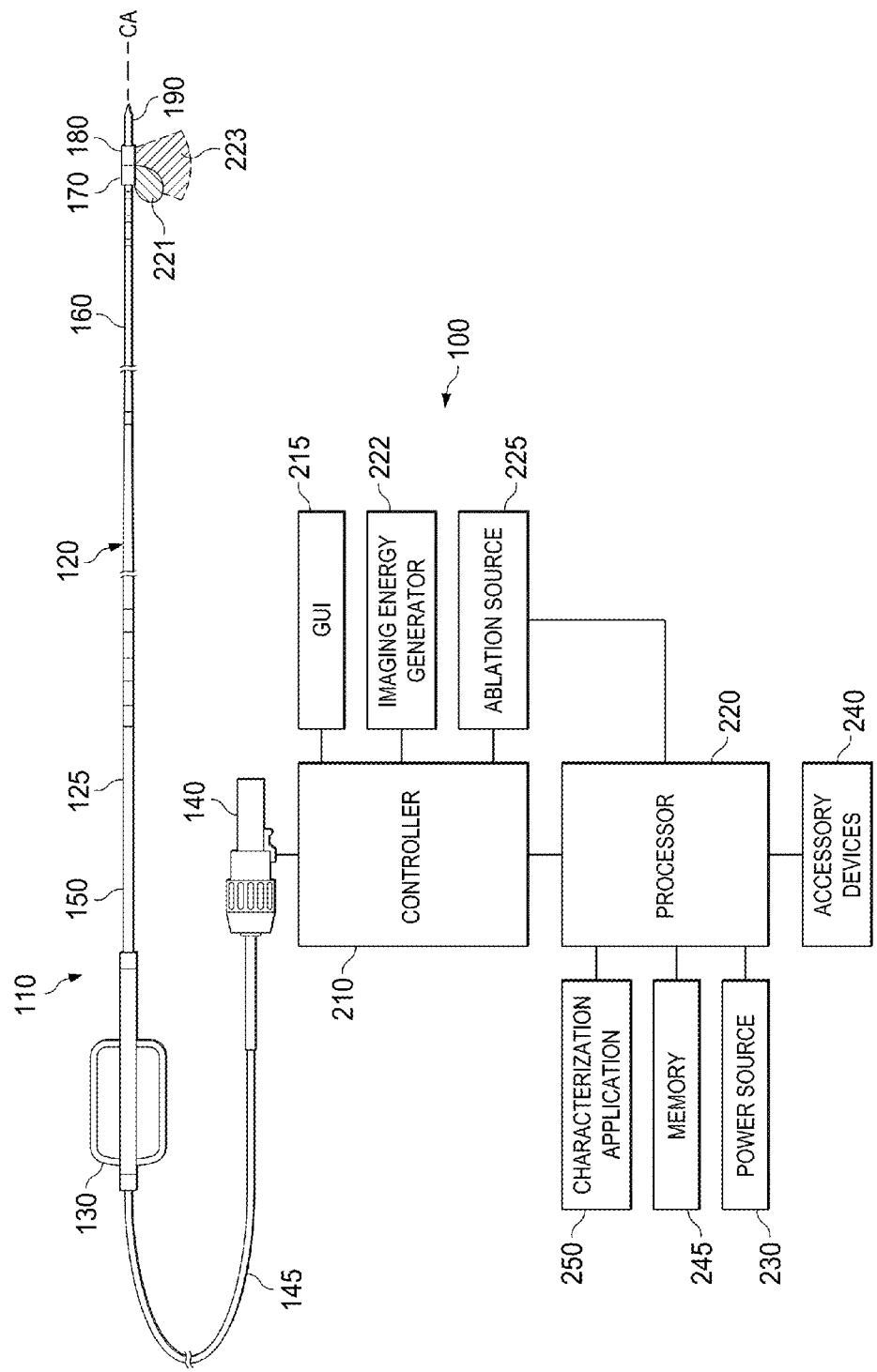

FIG. 1 is a schematic illustration of an adventitial tissue characterization system in accordance with one embodiment of the present disclosure.

Figure 2:
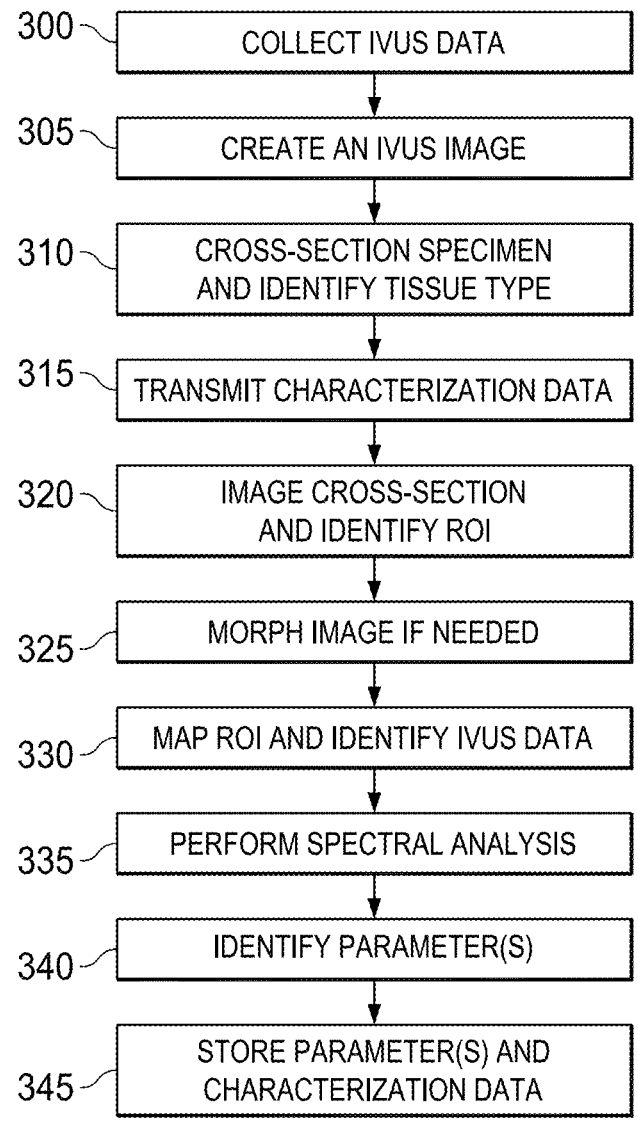

FIG. 2 illustrates an exemplary method of characterizing a specimen to populate a pattern recognition training database in accordance with one embodiment of the present disclosure.

Figure 3:
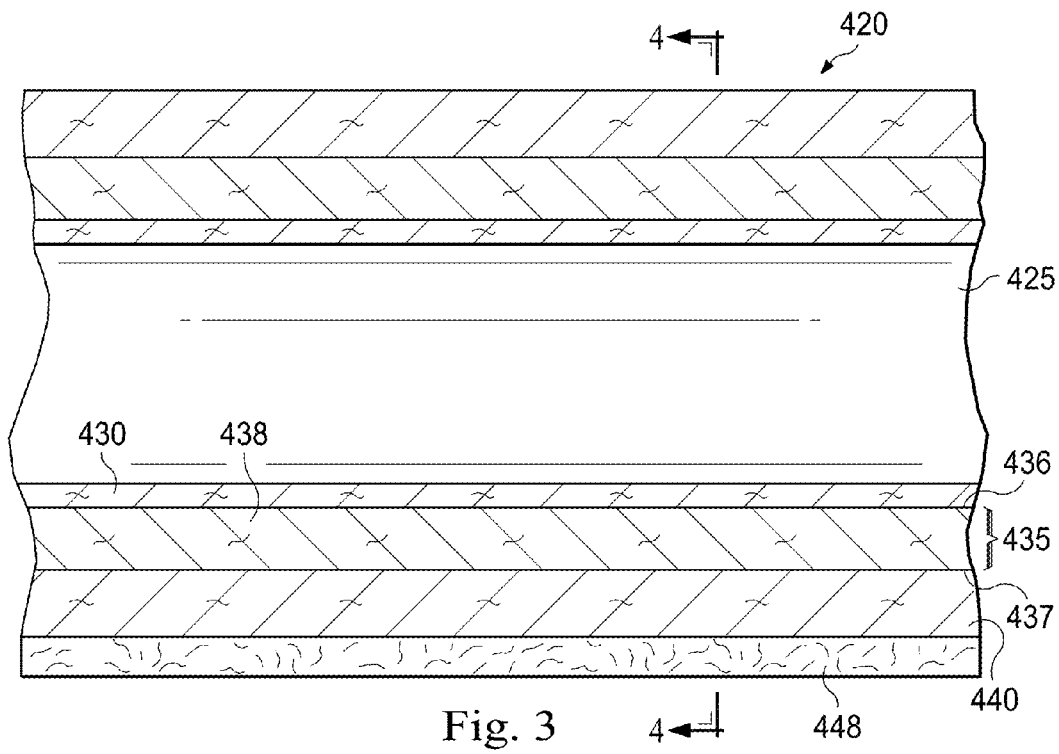

FIG. 3 is a diagrammatic, cross-sectional illustration of an unobstructed artery, showing vascular wall layers and perivascular supportive tissue.

Figure 4A:
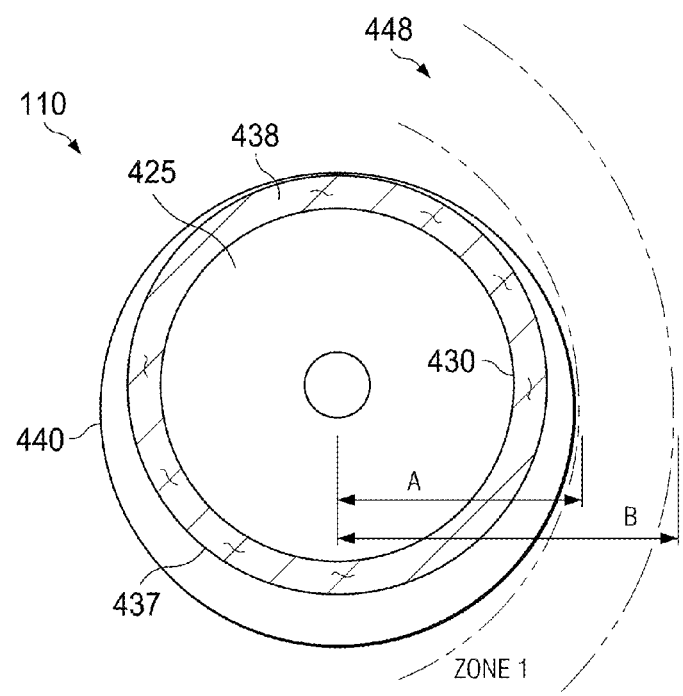
Figure 4B:
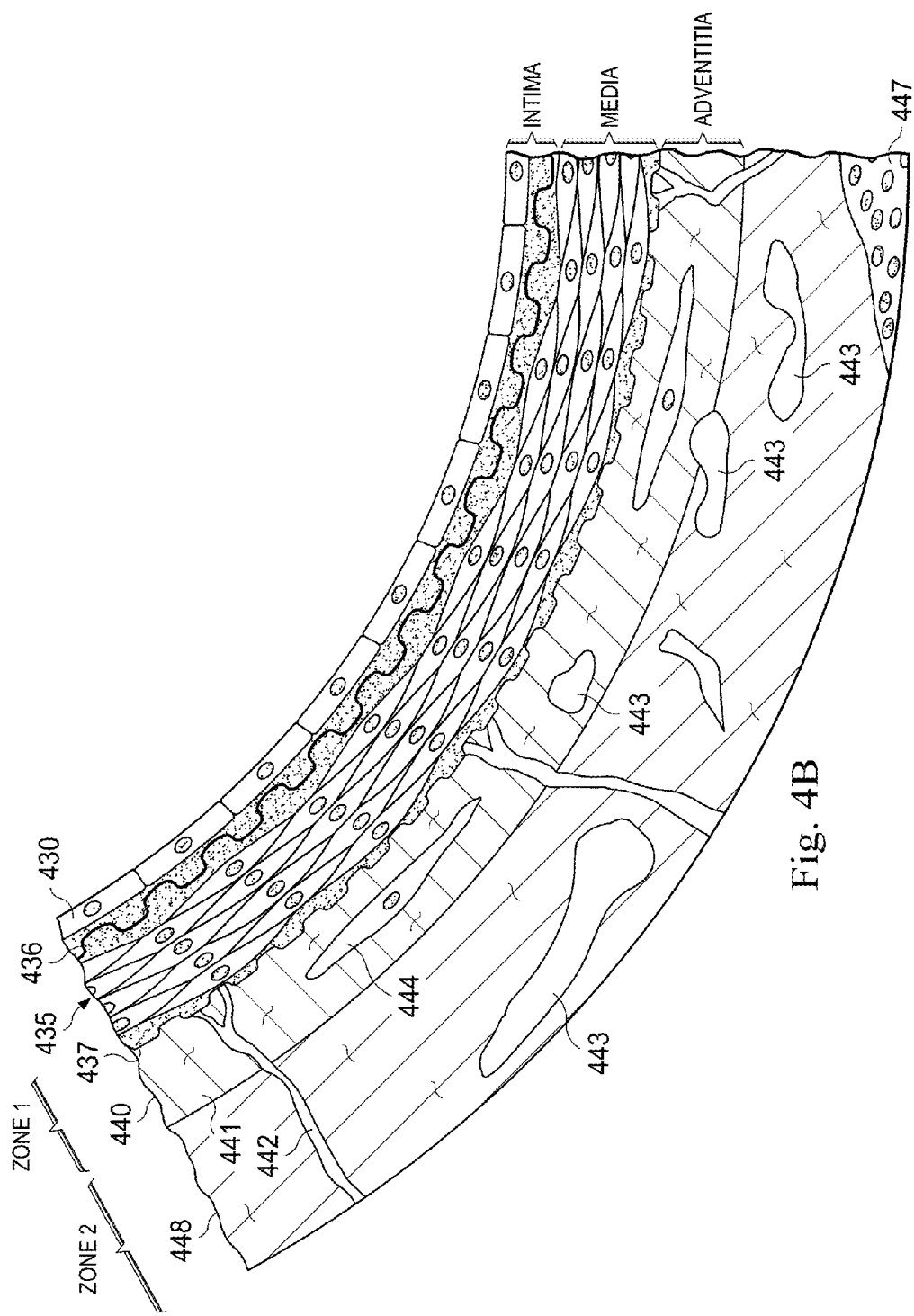

FIG. 4A is a transverse sectional illustration of the artery shown in FIG. 3 along the lines 4-4, with FIG. 4B being a partial enlarged view of FIG. 4A.

Figure 5:
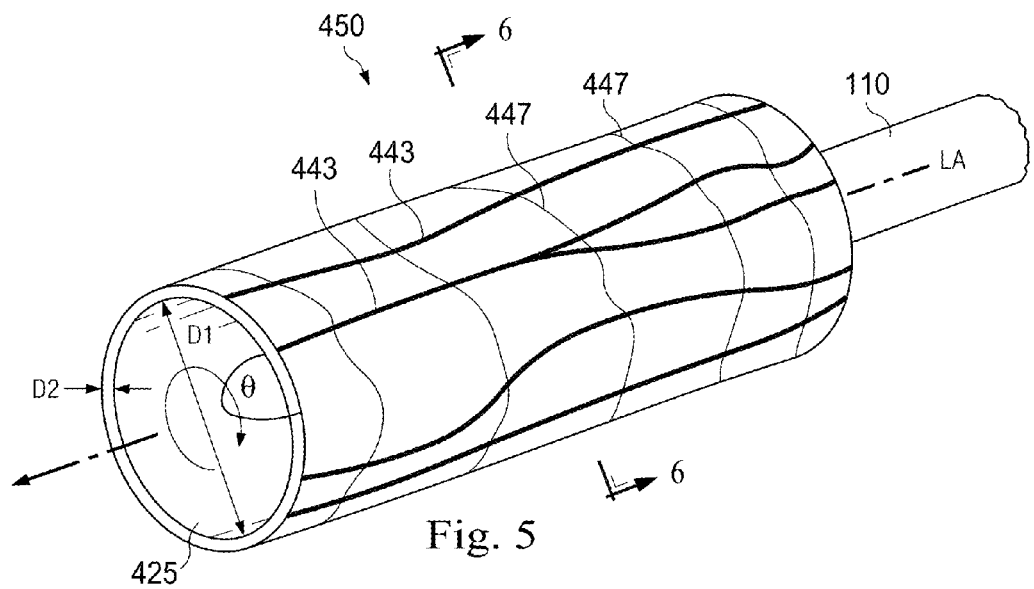

FIG. 5 is a diagrammatic, perspective illustration of a blood vessel showing nerve bundles extending within the perivascular tissue.

Figure 6B:
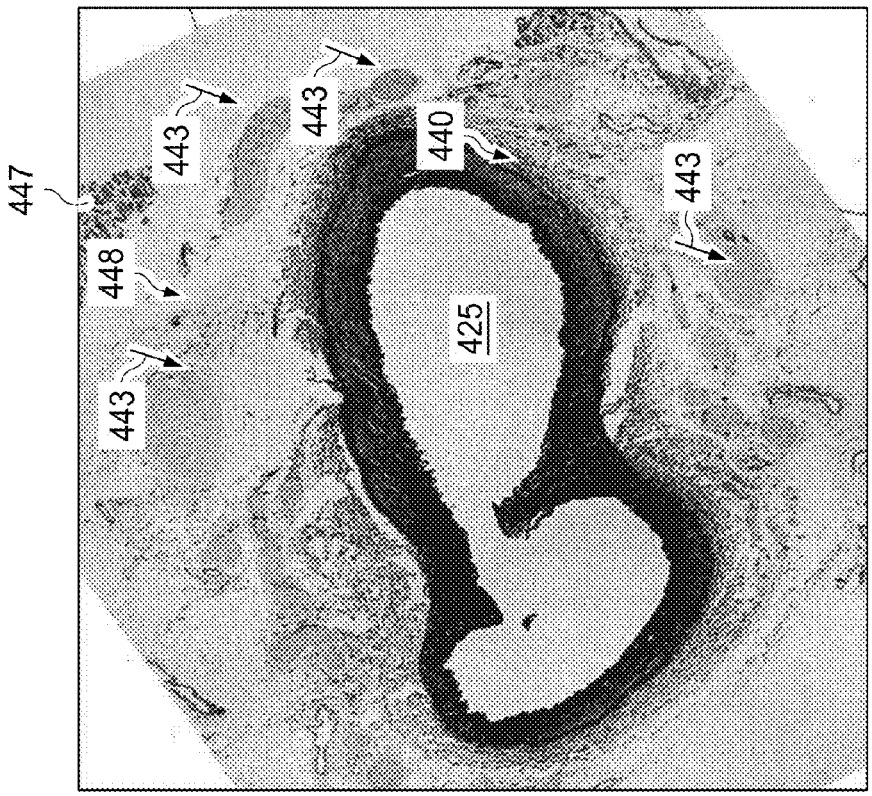
Figure 6A:
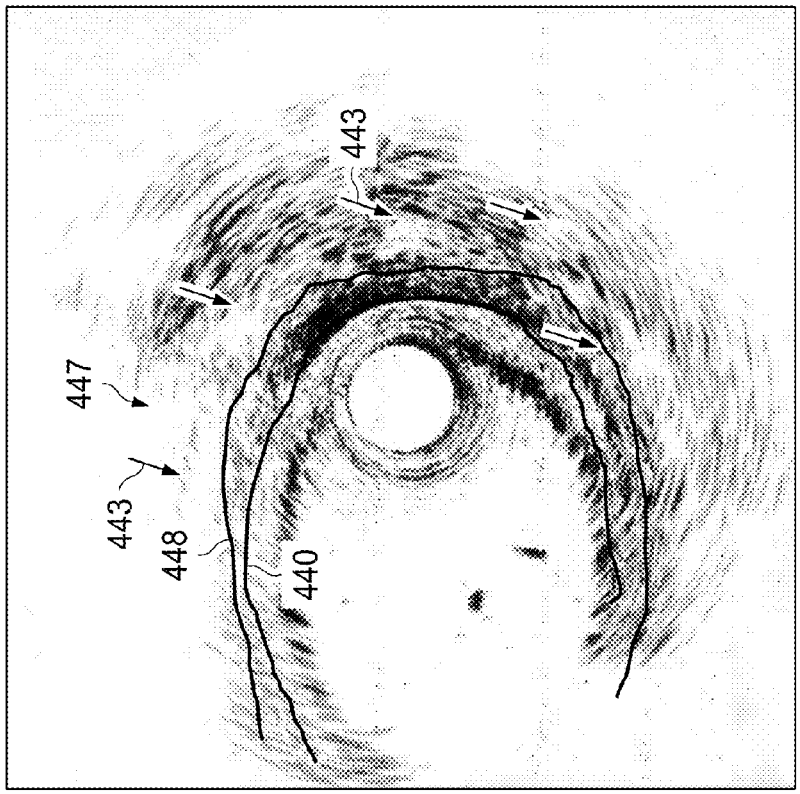

FIGS. 6A and 6B are cross sectional images taken along line 6-6 of FIG. 5, where 6A is an intravascular ultrasound image and 6B is the corresponding histology processed image with a MOVAT Pentachrome stain.

Figure 7:
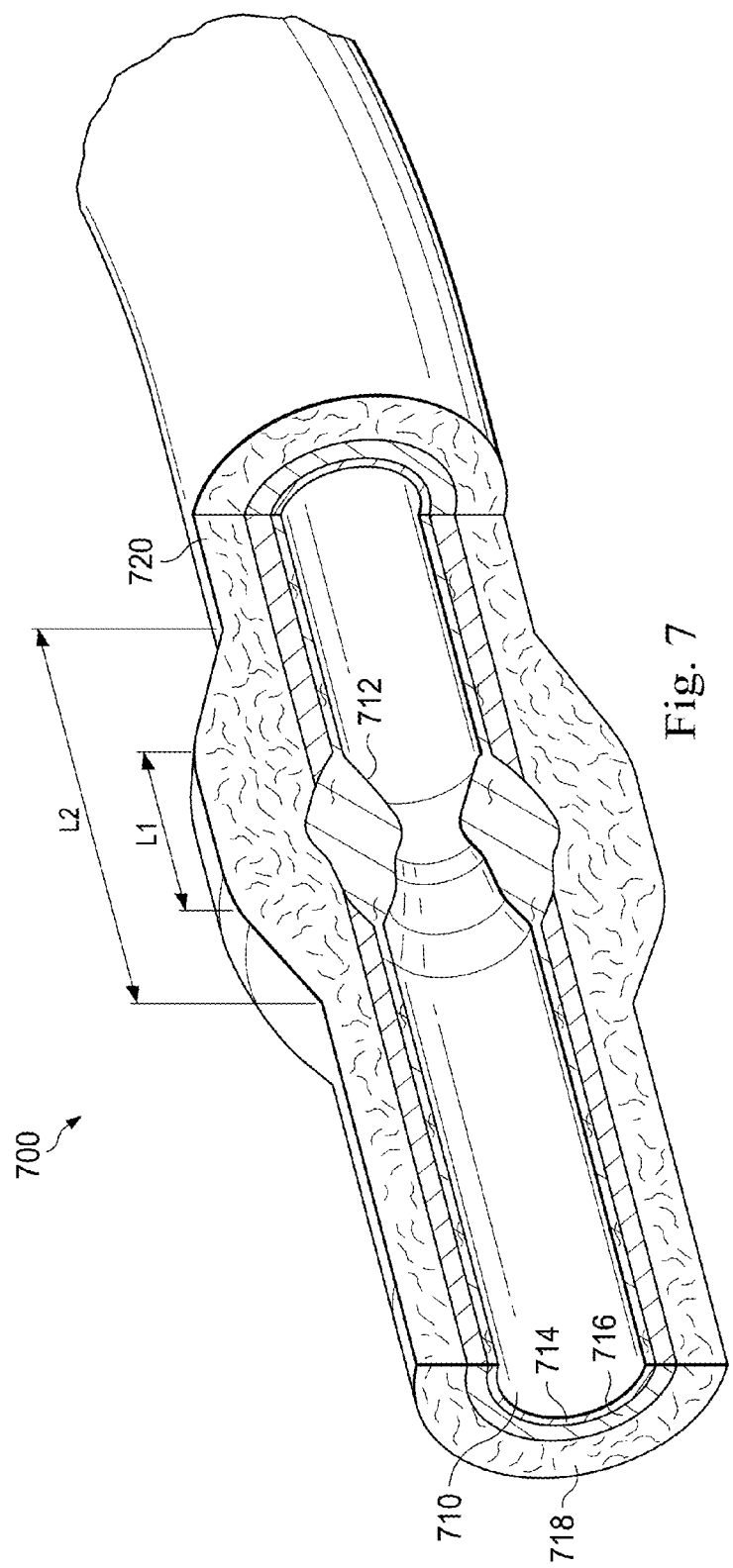

FIG. 7 is a diagrammatic, cross-sectional illustration of a partially obstructed artery.

Figure 8A:
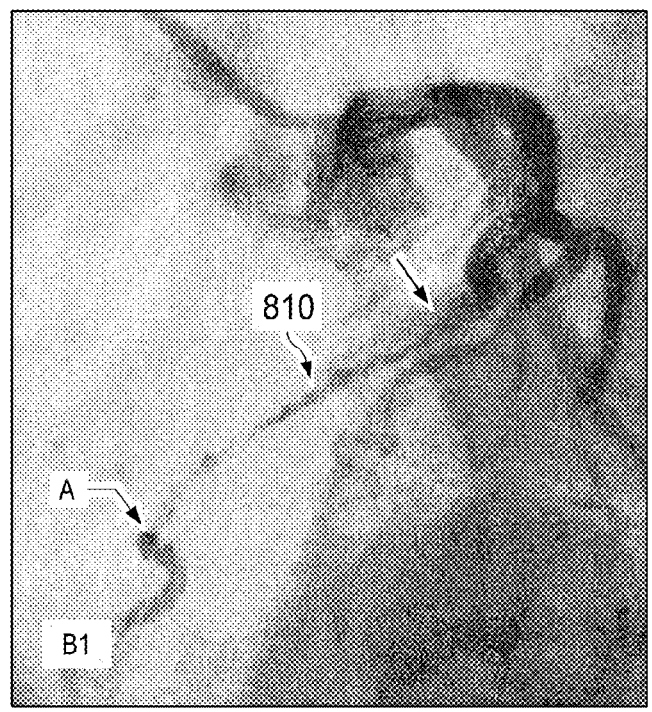
Figure 8B:
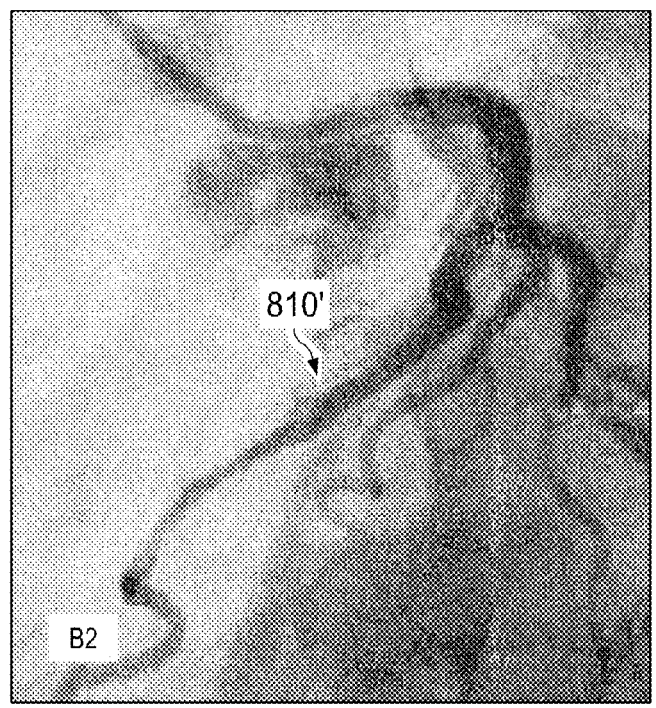

FIGS. 8A and 8B are angiographic images illustrating the effect of myocardial bridging on coronary arteries.

Figure 9A:
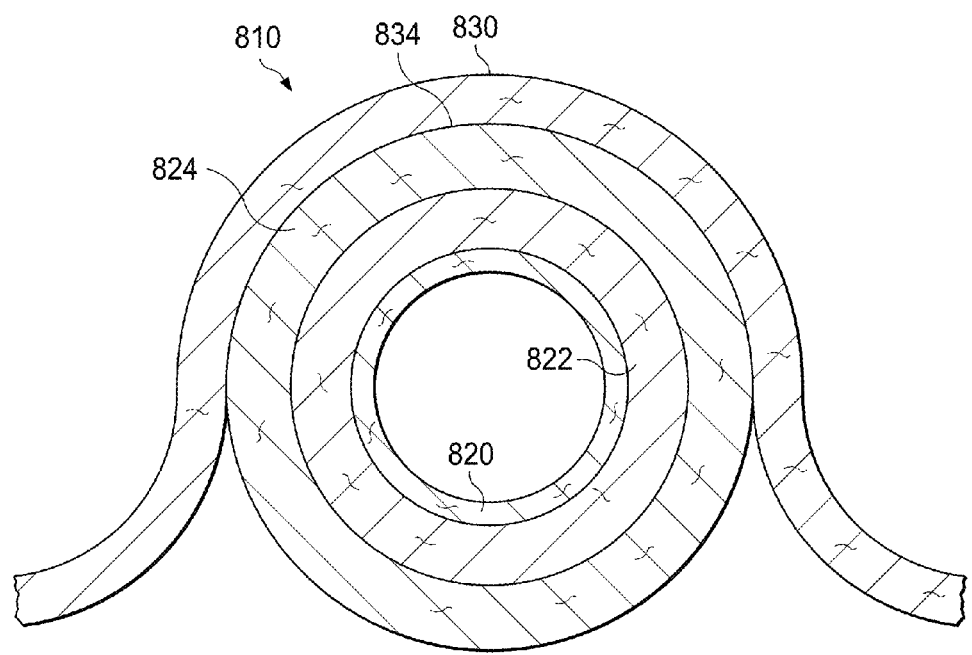
Figure 9B:
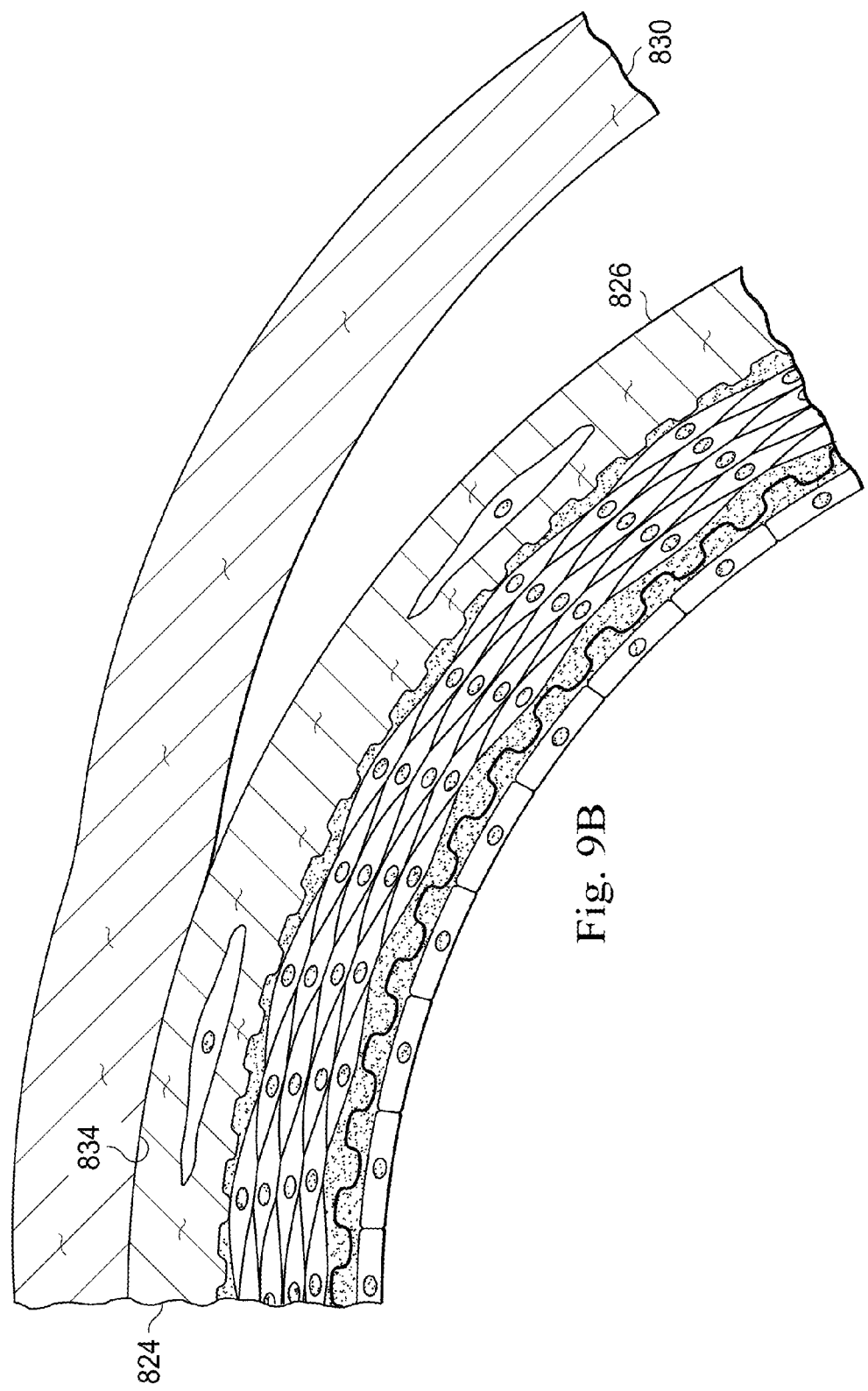

FIGS. 9A and 9B are diagrammatic, cross-sectional images of the coronary artery of FIG. 8A.

FIG. 10 is a diagrammatic, cross-sectional view of a stent disposed in a vessel.

Figure 11B:
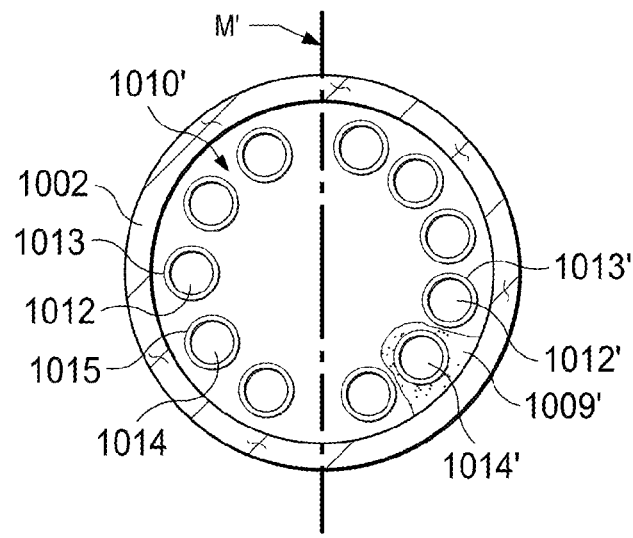
Figure 11C:
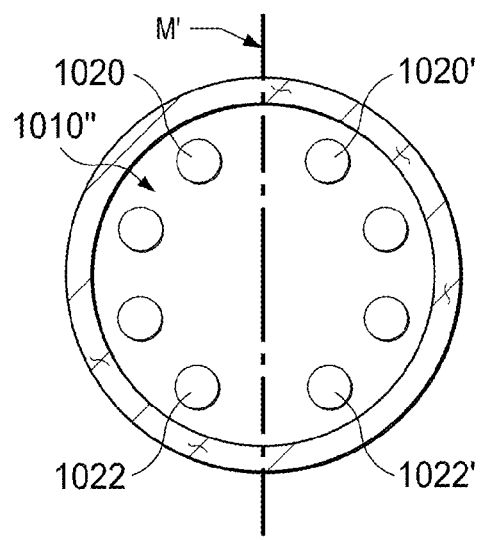

FIGS. 11A-11C illustrate axial cross-sectional views taken through the stent of FIG. 10 showing initial implantation conditions on the left and new conditions of the stent after a significant period of implantation on the right.

Figure 12A:
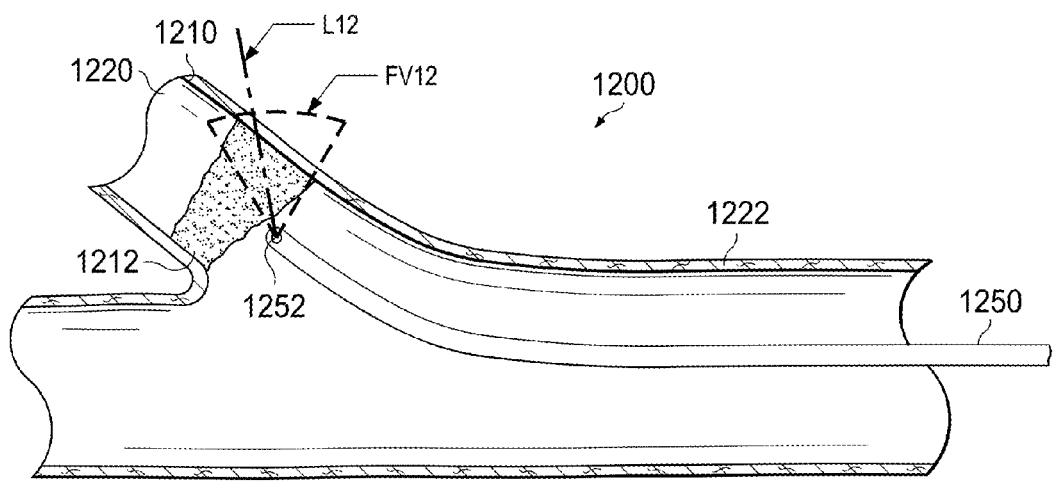
Figure 12B:
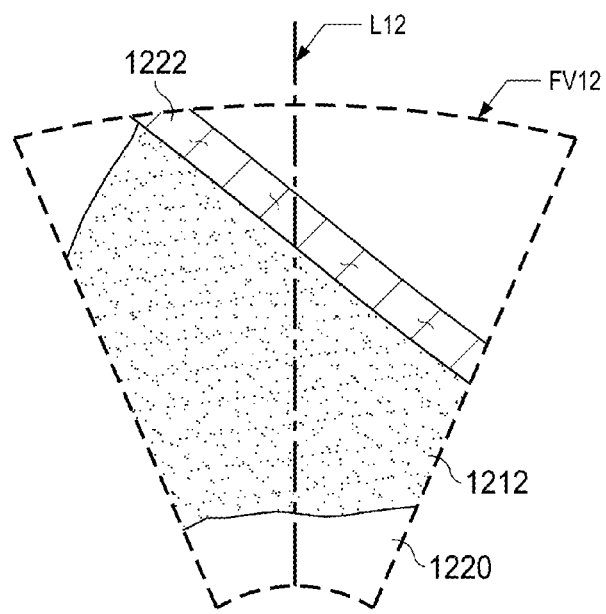

FIG. 12A illustrates an artery with a total occlusion and a catheter for imaging the occlusion, along with FIG. 12B showing the image of the occlusion generated by the catheter system.

Figure 13A:
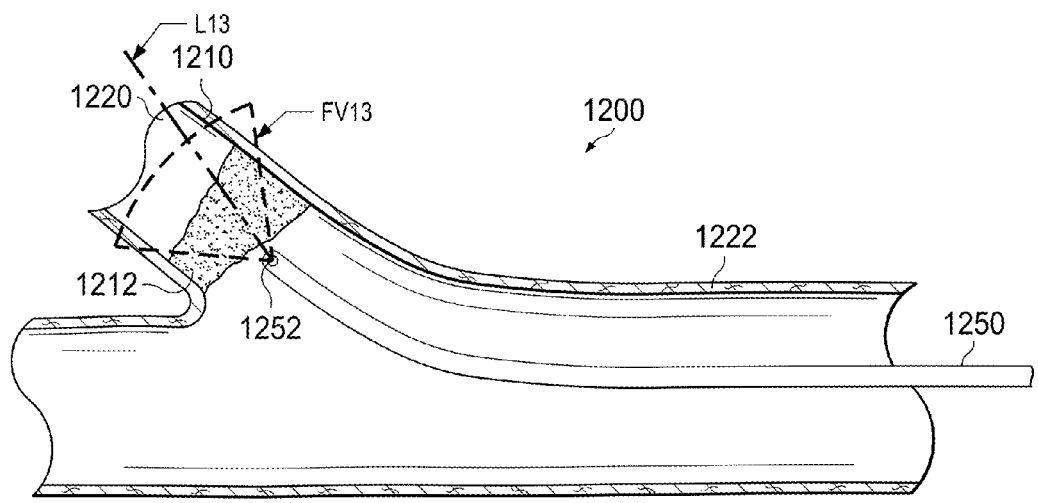
Figure 13B:
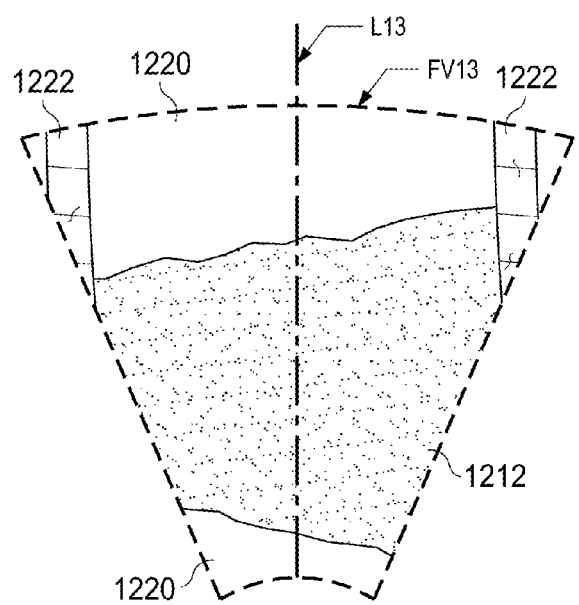

FIG. 13A illustrates an artery with a total occlusion and a catheter for imaging the occlusion, along with FIG. 13B showing the image of the occlusion generated by the catheter system.

Figure 14A:
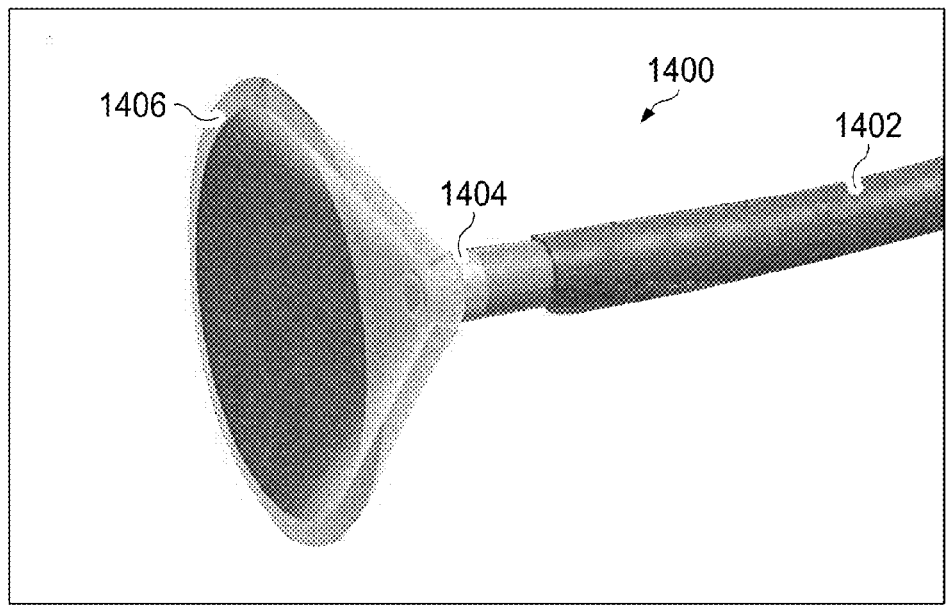
Figure 14B:
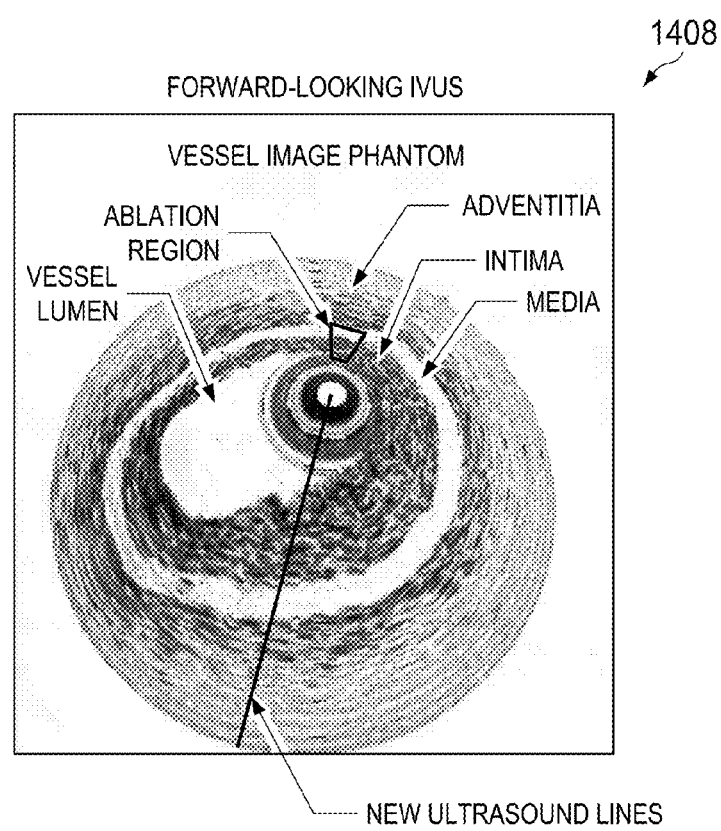

FIGS. 14A and 14B Illustrate a further forward looking imaging system and the resultant display according to another aspect of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to an apparatus, systems, and methods for image-guided diagnostic procedures and monitoring of therapy delivery procedures through adventitial tissue characterization. The present disclosure describes systems and methods for tissue characterization by analyzing images created by an energy emission device, such as, by way of non-limiting example, an ultrasound transducer, deployable with an imaging system to facilitate interpretation of images of vessel adventitial tissues, including ablated and neighboring tissue. The systems and methods described herein correlate image properties of the adventitial tissue with pre-determined tissue properties to automatically and reproducibly characterize the adventitial tissues in real time (i.e., as the tissues are being imaged and/or ablated). By automatically and reproducibly characterizing the adventitial tissues in real time, the systems and methods described herein minimize the known observer-variability associated with tissue characterization by observers. As used herein, unless expressly indicated otherwise, the adventitial tissues being referred to and characterized are the tissue layers immediately outside the media along with the perivascular supportive tissues surrounding the adventitia that include various intermingled tissue types generally within about 3-5 mm of the media that can include nerves, nerve bundles, blood vessels, muscle fibers (especially in the coronary arteries), connective tissue, fibroblasts and fat cells.

FIG. 1 illustrates an imaging system 100. The system 100 includes a catheter 110 comprising an elongate, flexible, tubular body 120 that is configured for intravascular placement and defines an internal lumen 125. The body 120 extends from a handle 130 along a longitudinal axis CA, which is coupled to an interface 140 by an electrical connection 145. The body 120 includes a proximal portion 150 and a distal portion 160. In FIG. 1, the distal portion 160 includes an ablative element 170 and an imaging apparatus 180 positioned proximal to a distal tip 190. The ablative element 170 and imaging apparatus 180 are positioned on a proximal segment of the distal tip 190. In the pictured embodiment, the ablative element 170 is positioned proximal to the imaging apparatus 180. In other embodiments, the ablative element 170 is positioned distal to the imaging apparatus 180. Generally, the catheter 110 may be configured to take on any desired profile, which may depend upon the type of ablative element, the type of imaging apparatus (e.g., ultrasound, OCT, multi-modality, etc.), the desired application, or the particular tissue of interest. In some embodiments, aspects of the catheter 110 may be substantially similar to aspects of a catheter disclosed in U.S. Publication 2011/0251487, titled "Apparatus and Methods for Intravascular Ultrasound Imaging and for Crossing Severe Vascular Occlusions," and published Oct. 13, 2011, which is incorporated by reference herein in its entirety.

The interface 140 is configured to connect the catheter 110 to a patient interface module or controller 210, which may include a graphic user interface (GUI) 215, such as a display or a touch screen. More specifically, in some instances the interface 140 is configured to communicatively connect at least the imaging apparatus 180 and the ablative element 170 of the catheter 110 to a controller 210 suitable for carrying out ablation and intravascular imaging. The controller 210 is in communication with and performs specific user-directed control functions targeted to a specific device or component of the system 100, such as the ablation catheter 110, the imaging apparatus 180, and/or the ablative element 170.

The interface 140 may also be configured to include a plurality of electrical connections, each electrically coupled to the ablative element 170 via a dedicated conductor and/or a cable (not shown), respectively, running through the lumen 125 of the body 120. Such a configuration allows for a specific group or subset of electrodes on the ablative element 170 to be easily energized with either monopolar or bipolar energy, for example. Such a configuration may also allow the ablative element 170 to transmit data from any of a variety of sensors on the ablative element via the controller 210 to data display modules such as a GUI 215 and/or a processor 220. The interface 140 is coupled to an ablation source 225 via the controller 210, with the controller 210 allowing energy to be selectively directed to the portion of the target tissue that is engaged by the ablative element 170.

In the pictured embodiment, the imaging apparatus 180 comprises an ultrasound imaging transducer. The imaging apparatus 180 can take the form of any one of a number of known ultrasound imaging transducers, such as, for example and without limitation, a phased array, a forward-looking array, a mechanically steered sector array, a rotational transducer, a vector array, a forward-looking oscillator transducer or a linear array. For example, in some embodiments involving cardiac ablation applications, the imaging apparatus comprises intracardiac echocardiography (ICE) or forward-looking ICE. The imaging apparatus has an imaging field of view 223 that may or may not overlap with the ablating field 221. In the pictured embodiment, the imaging field of view 223 is shown overlapping with the ablating field 221, thereby allowing the user to image the tissue being ablated within the ablating field 221 in real-time.

It should be appreciated that while the exemplary embodiments herein are described in terms of an ultrasonic imaging apparatus, or more particularly the use of IVUS data (or a transformation thereof) to render images of an object, the present disclosure is not so limited. Thus, for example, an imaging apparatus using backscattered data (or a transformation thereof) based on electromagnetic radiation (e.g., light waves in non-visible ranges such as Optical Coherence Tomography, X-Ray CT, infrared spectroscopy, etc.) to render images of any tissue type or composition (not limited to vasculature, but including other human as well as non-human structures) is within the spirit and scope of the present disclosure. Any form of imaging, measuring, and/or evaluation device (and resultant data) is within the spirit and scope of the present disclosure. Still further, while the system and techniques are described in the context of an invasive ultrasound system, it will be appreciated that the system and method of conducting tissue characterization may be accomplished throughout the body whether tissues are accessed through natural openings or through openings formed through the skin.

The controller 210 is connected to the processor 220, which is typically an integrated circuit with power, input, and output pins capable of performing logic functions, an imaging energy generator 222, and the ablation source 225. The processor 220 may include any one or more of a microprocessor, a controller, a digital signal processor (DSP), an application specific integrated circuit (ASIC), a field-programmable gate array (FPGA), or equivalent discrete or integrated logic circuitry. In some examples, processor 220 may include multiple components, such as any combination of one or more microprocessors, one or more controllers, one or more DSPs, one or more ASICs, or one or more FPGAs, as well as other discrete or integrated logic circuitry. The functions attributed to processor 220 herein may be embodied as software, firmware, hardware or any combination thereof.

The processor 220 may include one or more programmable processor units running programmable code instructions for implementing the ablative methods described herein, among other functions. The processor 220 may be integrated within a computer and/or other types of processor-based devices suitable for a variety of intravascular applications, including, by way of non-limiting example, ablation, intravascular imaging, and tissue characterization. The processor 220 can receive input data from the controller 210, a memory 245, a tissue pattern recognition database 250 usable for tissue characterization, accessory devices 240, the imaging apparatus 180, and/or the ablative element 170 directly or via wireless mechanisms. The processor 220 can interpret and use such input data to generate control signals to control or direct the operation of the catheter 110. In some embodiments, the user can program or direct the operation of the catheter 110 and/or the accessory devices 240 from the controller 210 and/or the GUI 215. In some embodiments, the processor 220 is in wireless communication with the imaging apparatus 180 and/or the ablative element 170, and can receive data from and send commands directly to the imaging apparatus 180 and/or the ablative element 170.

In various embodiments, the processor 220 is a targeted device controller that may be connected to a power source 230, accessory devices 240, the memory 245, and/or the ablation source 225. In such a case, the processor 220 is in communication with and performs specific control functions targeted to a specific device or component of the system 100, such as the imaging apparatus 180 and/or the ablative element 170, without utilizing user input from the controller 210. For example, the processor 220 may direct or program the imaging apparatus 180 and/or the ablative element 170 to function for a period of time without specific user input to the controller 210. In some embodiments, the processor 220 is programmable so that it can function to simultaneously control and communicate with more than one component of the system 100, including the accessory devices 240, the power source 230, and/or the ablation source 225. In other embodiments, the system includes more than one processor and each processor is a special purpose controller configured to control individual components of the system.

In the pictured embodiment, the controller 210 is configured to couple the imaging apparatus 180 to the imaging energy generator 222. In embodiments where the imaging apparatus 180 is an intravascular ultrasound (IVUS) transducer(s), the imaging energy generator comprises an ultrasound energy generator. Under the user-directed operation of the controller 210, the imaging energy generator 222 may generate a selected form and magnitude of energy (e.g., a particular energy frequency) best suited to a particular application. At least one supply wire (not shown) passing through the body 120 and the interface 140 connects the imaging apparatus 180 to the imaging energy generator 222. The user may use the controller 130 to initiate, terminate, and adjust various operational characteristics of the imaging energy generator 222.

The power source 230 may be a rechargeable battery, such as a lithium ion or lithium polymer battery, although other types of batteries may be employed. In other embodiments, any other type of power cell is appropriate for power source 230. The power source 230 provides power to the system 100, and more particularly to the processor 220. The power source 230 may be an external supply of energy received through an electrical outlet. In some examples, sufficient power is provided through on-board batteries and/or wireless powering.

The various peripheral devices 240 may enable or improve input/output functionality of the processor 220. Such peripheral devices 240 include, but are not necessarily limited to, standard input devices (such as a mouse, joystick, keyboard, etc.), standard output devices (such as a printer, speakers, a projector, graphical display screens, etc.), a CD-ROM drive, a flash drive, a network connection, and electrical connections between the processor 220 and other components of the system 100. By way of non-limiting example, a processor may manipulate signals from the imaging apparatus 180 to generate an image on a display device, may coordinate aspiration, irrigation, and/or thermal neuromodulation, and may register the treatment with the image. Such peripheral devices 240 may also be used for downloading software containing processor instructions to enable general operation of the catheter 110, and for downloading software implemented programs to perform operations to control, for example, the operation of any auxiliary devices attached to the catheter 110. In some embodiments, the processor may include a plurality of processing units employed in a wide range of centralized or remotely distributed data processing schemes.

The memory or database 245 is typically a semiconductor memory such as, for example, read-only memory, a random access memory, a FRAM, or a NAND flash memory. The memory 245 interfaces with processor 220 such that the processor 220 can write to and read from the memory 345. For example, the processor 220 can be configured to read data from the imaging apparatus 180 and write that data to the memory 345. In this manner, a series of data readings can be stored in the memory 245. The processor 220 is also capable of performing other basic memory functions, such as erasing or overwriting the memory 245, detecting when the memory 345 is full, and other common functions associated with managing semiconductor memory. In the pictured embodiment, the memory 245 comprises a database of characterization data.

The tissue pattern recognition or characterization application 250 is adapted to receive data (e.g., imaging data) from the processor 220 and/or the controller 210. The characterization application may exist as a single application or as multiple applications, and be locally or remotely stored. In an exemplary embodiment, the characterization application 250 is adapted to receive and store characterization data (e.g., tissue type, adventitial characteristics, ablation characteristics, stent characteristics, myocardium characteristics, and secondary parameters or patterns). In particular, to create a database of characterization data, after a tissue specimen has been imaged and IVUS data has been collected, a histology correlation is prepared by collecting, dissecting, and preparing the tissue specimen for slide review (e.g., fixing and staining the tissue specimen with a process that is well known in the art). Slide review allows a clinician to identify and characterize the tissue type(s) and/or histological chemicals/markers (i.e., chemicals and/or markers associated with particular tissue types) found within the specimen. It should be noted that the particular method used to characterize the tissue specimen is not a limitation of the present disclosure, and all tissue specimen characterization methods generally known to those skilled in the art are within the scope of the present disclosure.

In one embodiment, the tissue specimen comprises a region of ablated tissue. The tissue may be any of a variety of tissue types, including, by way of non-limiting example, muscle tissue, fatty tissue, fibrous tissue, fibrolipidic tissue, vessel tissue (e.g., by way of non-limiting example, compositional tissues such as vessel wall, luminal wall, medial-adventitial boundary, adventitial tissue, myocardium), neural tissue, calcific tissue, necrotic tissue, calcified-necrotic tissue, collagen compositions, cholesterol deposits, and/or adventitial tissue. In addition, the tissue specimen can comprise ablated tissue in any of a variety of stages of ablation, including, by way of non-limiting example, minimally ablated tissue, moderately ablated tissue, majorly ablated tissue, and/or completely ablated tissue. The characterization data gathered from the tissue specimens can include all other identifiable characteristics generally known to those of skill in the art. In some embodiments, tissue specimens having a full range of varying degrees of ablation per tissue type are interrogated (imaged and histologically sectioned) for inclusion in the characterization application 250.

The identified tissue type(s) and/or characterization conclusions are provided to the characterization application 250 as characterization data. In some embodiments, the characterization data is provided via the GUI 215 or another input device that is electrically coupled to the controller 210 and/or the processor 220. The characterization data is then stored in the memory or database 245.

In one embodiment, the characterization application 250 is adapted to create a histology image of the tissue specimen and to identify the at least one corresponding region on an image (e.g., an IVUS image) of the tissue specimen. A region of interest (ROI) on the histology image (which may be provided to the characterization application 250 via the GUI 215 or another input device in the form of digitized data that is used to create the histology image) can then be identified by the user. The ROI may be characterized by the characterization data, and can comprise the whole tissue specimen or only a portion thereof. The characterization application is adapted to identify a corresponding region on the scanned image (e.g., IVUS image).

In some instances, the histology image may need to be morphed or warped to accurately match and substantially fit the contour of the IVUS image (thereby removing histological preparation artifacts). In some embodiments, therefore, the characterization application 250 is adapted to morph or warp the histology image to accurately match the IVUS image. Specifically, the characterization application 250 is configured to identify at least one landmark common to both the histology image and the IVUS image and is adapted to use various algorithms to substantially align the two images. The landmark may comprise an anatomic landmark (such as, by way of non-limiting example, side-branch vessels, a vessel wall, and a tumor border) or a marker (such as, by way of non-limiting example, a suture tie or an inked mark). In one embodiment, the characterization application is adapted to use a first algorithm (e.g., a morphometric algorithm) to substantially align the corresponding landmarks and a second algorithm (e.g., a thin plate spline (TPS) deformation technique) to substantially align the non-landmark portions of the object.

In one embodiment, the characterization application 250 is further adapted to determine and store at least one parameter associated with the ROI portion of the IVUS image. In particular, the characterization application 250 is adapted to identify the IVUS data (i.e., the raw backscatter data) that corresponds to the ROI identified on the IVUS image (i.e., the IVUS data that was originally used to create the ROI on the IVUS image). Different types and densities of tissue absorb and reflect emitted energy differently. Each reflected signal is characteristic of the type of tissue and the condition of the tissue that reflected it. Differences in the reflected signal along each path can be determined by performing analysis on the signals. As a result, identifying different signal characteristics along each reflected path allows for a correlation to the type of tissue and the condition of the tissue associated with those particular signal characteristics. As will be described below, the signal characteristics of each reflected signal can serve as a signature for different types of components within the scanned tissue, including, for example and without limitation, necrotic plaque components within an artery, adventitia, neural tissue, minimally ablated muscle tissue, or completely ablated neural tissue.

The at least one parameter is then stored in the memory 245, where it is linked to the characterization data associated with the ROI. Each parameter may be associated with more than one tissue type or degree of ablation. For example, a first parameter may be common to multiple tissue types and multiple degrees of ablation. In some embodiments, signal analysis (i.e., frequency analysis, etc.) is performed on the identified IVUS data before the parameters are identified because the frequency information can serve as a "signature" for a particular tissue type or characteristic. The IVUS data may be converted or transformed into the frequency domain to identify the specific frequency spectrum of the ROI. The characterization application 250 and this transformation process are described in further detail below with reference to FIG. 3.

It should be appreciated that the number and location of the components depicted in FIG. 1 are not intended to limit the present invention, and are merely provided to illustrate an exemplary environment in which the catheters, systems, and methods described herein may operate. Thus, for example, a system having a plurality of databases and/or a remotely located characterization application is within the spirit and scope of this disclosure.

An exemplary method of populating the training database or memory 245 is illustrated in FIG. 2. Specifically, at step 300, IVUS data (i.e., RF backscatter data) is collected from a portion of the specimen. This data is used to create an IVUS image, which may be a two dimensional image or a three dimensional image, at step 305. At step 310, the scanned portion of the specimen is dissected and/or cross-sectioned and a tissue type (and/or characterizations thereof) is identified. At step 315, this characterization data is transmitted to the tissue characterization system 100. In particular, the characterization data may be transmitted to the memory 245 and/or the characterization application 250. The characterization data may include a variety of identifying and/or characterization information, such as, for example and without limitation, information about the type of tissue, the different cell components within the tissue, particularly within the adventitial tissue, and the degree of ablation (e.g., varying cellular changes due to ablation). As a further feature, IVUS data may be collected for an unablated ROI and compared to an existing database to obtain an initial characterization. Ablation energy can then be applied to the ROI to change the nature of the tissue in the ROI. Then, the ROI tissue may be dissected and/or cross-sectioned. At step 320, an image of the cross-sectioned object is created and an ROI is identified (e.g., by a user and/or the processor 220). The image may be two-dimensional or three dimensional. At step 325, this image may be morphed, if needed, to substantially match the cross-section image to the IVUS image formed at step 305. This may include identifying and matching up at least one common landmark on the two images using an algorithm, as described above. At step 330, the ROI is mapped to the IVUS image and associated IVUS data is identified. Image analysis (including, for example and without limitation, spectral analysis and frequency analysis) is then performed on the associated IVUS data at step 335, and at least one parameter or pattern is identified at step 340. At step 345, the at least one parameter and the characterization data is stored in the memory 245 and/or the characterization application 250. In some embodiments, the at least one parameter or pattern is stored such that it is linked to the characterization data.

The process depicted in FIG. 2 is repeated for each tissue component or section desired to be identified and/or characterized, and may be repeated for each component as many times as desired in order to obtain an accurate range of signal properties. Still further, in one aspect, tissue characterization is performed with a stent in place such that the characteristics of the stent can be accounted for in the images.

FIGS. 3, 4A, and 4B illustrate the layers of a normal artery 420. The innermost layer that defines the lumen 425 of the artery 420 comprises the intima 430. In a healthy artery, the intima is relatively thin. As plaque develops and infiltrates the intima, it increases in thickness. Medial layers 435 surround the intima 430. The medial layers 435 include smooth muscle tissue and provide structural integrity for the artery 420. The medial layers are made up of three layers that include two elastic layers, an inner elastic lamina 436 and an outer elastic membrane 437, along with a thicker muscular media comprised of smooth muscle cells 435. The outermost layer is the adventitia 440, which typically comprises fibrous tissue such as collagen, and has a poorly defined outer boundary transitions to perivascular supportive tissue 448. As shown in more detail in the enlarged partial vessel view shown in FIG. 4B, the adventitia includes a collagen material 441 interrupted by small blood vessels or arterioles 442, such as vasa vasorum or neo vasa vasorum, that supply oxygen to the main artery wall and typically extend the inside the media or at the edge of the medial-adventitial border. In higher numbers or size than normal, they are considered to be indicative of disease progression and vulnerability. In addition, nerve bundles 443 and fibroblasts 444 also exist within the collagen material 441. The perivascular tissue 448 surrounds at least a portion of the adventitia and can include various intermingled tissue types generally within about 3-5 mm of the media that can include nerves, nerve bundles 443, blood vessels, muscle fibers 447 (especially in the coronary arteries), connective tissue, fibroblasts and fat cells. As shown in FIG. 4b, some structures such as nerve bundle 443 can extend within both adventitia 440 and within perivascular tissue 448.

Referring more specifically to FIG. 4A, an imaging device 110 is shown positioned within the vessel lumen 425. In traditional arterial tissue characterizations, the imaging device supplies return data concerning the intima 430 (along with any plaques) and the media 438. However, approximately 45% of the nerves associated with a blood vessel can be located by extending the tissue characterization outwardly to an initial area designated as Zone 1. This includes the adventitia along with a small portion of perivascular tissue. For example in a large artery having an internal diameter of 5 mm, such as a renal artery, Zone 1 may extend to a radius A of approximately 3.5 mm or a 7.0 mm diameter. In a further aspect, by expanding the tissue characterization area to include the perivascular tissue of Zone 2, approximately 95% of the nerves and nerve bundles can be image and characterized. In the large artery having an internal diameter of 5 mm, the Zone 2 diameter would extend to approximately 11.0 mm with a radius B of approximately 5.5 mm. As explained more fully below, characterization of the tissue beyond the external elastic lamina or outer elastic membrane 437 provides additional information that may assist in diagnosing and treating any number of vascular or neurologic diseases or conditions. As used herein, unless expressly indicated otherwise, the adventitial tissues being referred to and characterized are the tissue layers immediately outside the outer elastic membrane 437 along with the perivascular tissues surrounding the adventitia that include various intermingled tissue types generally within about 3-5 mm of the outer elastic membrane that can include nerves, nerve bundles, blood vessels, muscles (especially in the coronary arteries), connective tissue, fibroblasts and fat cells.

With reference back to FIG. 1, the data collected by the imaging apparatus 180 of the catheter 110 is initially in the form of raw data of the reflected signals along each scan line. The data is then refined or transformed into a format that can be analyzed by the characterization application 250 to determine various signal characteristics that may identify associated tissue types within and adjacent the scanned object 405. In the pictured embodiment, the characterization application 250 includes several component parts, including the memory or database 245, a signal analyzer logic, and a correlation logic. The signal analyzer logic is configured to process and analyze the data to identify, in real-time, the various components of the scanned object 405. The signal analyzer logic is configured to identify various types of tissue and/or tissue components and to provide an assessment as to the content and health of the adventitia based on the type of tissues and/or tissue components identified. In addition, adventitial tissue characterization can be performed before delivery of a therapy, such as ablation, and after delivery of a therapy to provide the user with feedback on the impact of the therapy on the structures of the adventitia. Additional details concerning systems that provide both imaging and therapy delivery can be found in U.S. Provisional Application No. 61/745,476, filed Dec. 21, 2012, entitled: Device, System, and Method for Imaging and Tissue Characterization of Ablated Tissue and U.S. Provisional Patent Application No. 61/733,738, filed Dec. 5, 2012, entitled: System and Method for Non-Invasive Tissue Characterization, each of which is hereby incorporated by reference in their entirety.

Referring now to the example shown in FIG. 5, the imaging apparatus 110 is positioned within the lumen 425 of the vessel 450. The lumen 425 has an internal diameter D1 and a vessel wall thickness extending between D1 and the outer diameter D2. As explained above, the internal diameter D1 can be approximately 5 mm and external diameter D2 can be approximately 11 mm, making the wall thickness approximately 3 mm. In the illustrated example, the vessel 450 is a renal artery with perivascular tissue including sympathetic renal nerves 443 extending along the vessel. In addition, smooth muscle cells 447 may also extend within the perivascular tissue. In embodiments using ultrasound imaging, the transducers of the imaging apparatus 110 would be pulsed along scan lines and then acquire echoes of backscatter signals reflected from the tissue along each scan line. The backscatter signal is characteristic of the type of tissue (including the tissue composition and level of ablation if utilized) that reflected it. Differences in the backscatter signal along each scan line can be determined by performing a frequency analysis, using spectral analysis and autoregressive coefficients, a wavelet decomposition, and/or a curvelet decomposition on the signals. As a result, identifying different signal characteristics along each scan line allows for a correlation to the type of tissue and, in the presence of ablation, a certain level of ablation associated with those particular signal characteristics. As further described herein, signal characteristics of the backscattered signal can serve as a signature for different types of components of the adventitial tissues of the vessel, including, for example, nerve bundles, blood vessels, myocardium or other muscle, and fibroblasts.

The signal properties of the transmit and receive signals are processed by the characterization application 250, which is configured to correlate the signal properties of the scan line segment with the type of tissue component having those or similar signal properties. In that regard, the characterization application 250 is configured to compare and match the signal properties to pre-determined or pre-generated adventitial tissue signal properties contained within the memory or database 245. Various parameters may comprise the database of pre-determined tissue signal properties. The parameters comprising the database 245 would be pertinent to both the desired application or tissue-of-interest and the imaging modality of the imaging probe (i.e., ultrasound, OCT, spectroscopy, etc.). The characterization application 250 is configured to recognize the type of imaging modality employed by the imaging probe 110 and to use the appropriate pre-determined tissue signal properties associated with that particular imaging modality. For example, if the imaging modality being used were ultrasound, the pre-determined signal properties may include various parameters in the spectral domain directly associated with scatter size, density, viscosity, and their acoustic properties such as impedance and attenuation coefficient. The pattern recognition training database also contains macro-data about overall characteristics, such as size, nerve cell directionality, vasa vasorum directionality, morphology, as well as patient demographic information such as age, gender, race and relevant medical history, such as known diabetic, cardiovascular disease, hypertension information and others.

In some embodiments, the imaging system 100 may employ a multitude of different imaging modalities to image the same object such as blood vessel 450. In some embodiments, these imaging modalities are used sequentially, whereas in other embodiments, the different imaging modalities are used simultaneously (e.g., using a multi-modality imaging apparatus). In one example, the imaging probe is first energized to image the adjacent tissue of the vessel with a 40 MHz ultrasonic pulse. Following the first imaging pass of the probe, the imaging probe is energized to image the adjacent tissue with a 20 MHz ultrasonic pulse. In such a system, the image data from both passes may be compared to corresponding data in by the characterization application 250. In still a further aspect, the imaging probe may be constructed to provide and detect harmonic variations of the center frequency such that different frequencies can be detected within a single pulse. In still a further embodiment, the imaging probe 110 may be configured to image the object using a multitude of different imaging modalities (e.g., OCT and ultrasound). In some embodiments, the characterization application 250 is configured to combine or analyze the pre-determined signal properties and patterns associated with each imaging modality used to perform adventitial tissue characterization.

Secondary parameters may be included within the data structure to reflect the type of tissue and/or the particular pre-existing conditions or differential diagnoses of the patient. The secondary parameters may be utilized by the correlation logic to more accurately compare and match the signal properties to the pre-determined signal properties 480. One secondary parameter may comprise the type of vessel being observed. For example, in larger vessels the vessel walls may be much thicker and the overall diameter of the vessel may be much larger. Thus, it is anticipated that the imaging device may need to be positioned closer to one wall within a large vessel to perform adventitial tissue characterization on only a portion while in a smaller vessel, such as a coronary artery, it may be possible to perform adventitial tissue characterization on the full circumference of the adventitial tissue. In some embodiments, the imaging system 100 can determine the type of tissue or anatomic region observed with the vessel and use this as a secondary parameter before automatically selecting the appropriate pre-determined signal properties associated with the type of tissue or anatomic region or appropriately adjusting the pre-determined signal properties to reflect the type of tissue or anatomic region. In other embodiments, the user may enter the type of tissue or anatomic region manually (e.g., via the GUI 215), and either the user or the imaging system 100 may select the appropriate pre-determined signal properties associated with that type of tissue/region or appropriately adjust the pre-determined signal properties to reflect this type of tissue/region. For example, if the tissue being scanned includes a calcified vascular plaque, either the user or the imaging system 100 may select the appropriate pre-determined signal properties associated with calcified plaque tissue or appropriately adjust the pre-determined signal properties to reflect changes observed for calcified plaque tissue. In some embodiments, a three-dimensional data set can be constructed with the imaging apparatus 110 to provide further parameters related to tissue type and matched back to the secondary parameters in the database 245 that contains these pre-determined ablation values for various tissue types.

Another secondary parameter associated with the imaging may comprise the particular frequency or harmonics employed by the imaging apparatus 110. For example, the database 245 may contain particular sets of pre-determined signal properties associated with particulars frequencies or harmonic patterns.

With reference again to FIG. 2, the data collected by the imaging apparatus 180 is initially in the form of raw ultrasound data of the backscattered signals along each scan line. The ultrasound data is then analyzed to determine various signal characteristics that may identify associated tissue types. The signal analyzer logic is configured to process and analyze the data to identify, in real-time, the presence and components of the adventitial tissue. Because different types and densities of tissue absorb and reflect the ultrasound pulses differently, the signal analyzer logic utilizes the reflected backscatter data to assemble a two-dimensional or three-dimensional ultrasound characterization of the adventitia from hundreds of pulse/acquisition cycles. In this embodiment, the logic is configured to identify various types of adventitial tissue, including vasa vasorum, nerve bundles, collagen matrix and strands of muscle cells (particularly in the case of coronary arteries) within the adventitial tissue.

In one embodiment, the signal analyzer logic includes logic to transform the data to the frequency domain and analyze frequency information of the signals to determine one or more signal properties. It will be appreciated that the signal analyzer logic may be embodied as part of an ultrasound imaging console, an ablation system console, or as part of a separate system that receives raw radio frequency data from an ultrasound apparatus. If the radio frequency data is in analog form, a digitizer may be provided to digitize the data. A signal processing logic is configured to process each scan line of the ultrasound data and transform it to a format that can be analyzed. To reduce processing time, a border detection or segmentation logic may be used to determine the location of the borders of the object being scanned, particularly the border between the media and the adventitia such that the characterization application 250 can focus on analyzing the echo returns from adventitial tissue extending beyond the media including the perivascular tissues. Because the analysis is most interested in the components of the adventitial tissue, scan line data outside of the adventitial tissue can be filtered and removed. One example of a border detection system is described in U.S. Pat. No. 6,381,350, entitled "Intravascular Ultrasonic Analysis Using Active Contour Method and System," which is incorporated herein by reference for all purposes.

After border detection, the scan line data is transformed. Of course, border detection can be performed after transformation. Transformation logic is configured to transform the remaining scan line data into a format suitable for analysis. In general, the transformed format should match the same format used to build the pre-determined signal properties of the object component. In one embodiment, the transformation logic transforms the data to a power spectrum plot of frequency versus power output. Various transformation algorithms include a Fourier transformation, Welch periodograms, and auto-regressive modeling. Other types of transformations can include transforming the data to wavelets that provide an image with frequency and time information. For example, other signal processing techniques may include wavelet decomposition or curvelet decomposition to deliver parameters that are relevant to discrimination between tissue types while not being influenced by the system transfer function of the imaging system and probe. Another transformation includes using impedance, rather than frequency, which gives an image of acoustic impedance. In this format, different tissue components have different impedance properties that provide different signal reflections.

Referring to FIG. 2, a spectral analysis logic analyzes the power spectrum of the scan line data to determine its spectral properties in step 335. As mentioned previously, spectral properties or parameters may include maximum power, frequency at the maximum power, minimum power, the frequency at the minimum power, the slope, y-intercept, mid-band fit, and integrated backscatter. The spectral parameters are identified in step 340 and are then inputted to a classification application 250 that attempts to classify the spectral parameters associated to a particular scan line segment with previously measured spectral parameters from a known tissue component. As mentioned above, the signal analyzing techniques need not be limited to spectral analysis and autoregressive coefficients, but could entail use of wavelet decomposition or curvelet decomposition to deliver parameters that may be used by the classification logic to discriminate between tissue types.

A variety of pattern recognition approaches may be used by the classification logic and/or correlation logic. For example, the database 245 of relevant secondary parameters and pre-determined tissue signal properties could be the starting point of various pattern recognition approaches, covering, but not limited to, classification trees, random forests, neural networks, regression trees, principal components, and/or a combination of these to arrive at an accurate tissue characterization. For example, in one embodiment, the pre-determined tissue signal properties and/or the secondary parameters may be stored in the database 245 as a classification tree or a regression tree having branch node conditions based on the pre-determined tissue signal properties and one or more leaf nodes that identify a tissue component of adventitial tissue. In another embodiment, the pre-determined tissue signal properties may be embodied in the database as an artificial neural network having one or more nodes that identify a tissue component of adventitial tissue. In some embodiments, the classification logic and/or the correlation logic may utilize a random forest classifier to analyze a number of classification trees (e.g., different classification trees based on different pre-determined signal properties or based on a multitude of different imaging modalities) to arrive at a tissue characterization.

The characterization application 250 may be configured to reconstruct the received data into displayed 2D or 3D images, and the identified adventitia components may be visually distinguished on a display associated with the GUI 215. In some embodiments, a display may be included as a component of an imaging system console (not shown). In other embodiments, the display may be an independently located device that communicates either wirelessly or through a wired connection with the characterization system 100. In some embodiments, the display may be remotely located.

Referring now to FIGS. 6A and 6B, there are shown cross-sectional images of the vessel of FIG. 5 taken along line 6-6. FIG. 6A illustrates an exemplary IVUS image showing the inner lumen 445, nerve bundles 443 and muscle fibers 447 disposed in the adventitial tissue. A pair of lines has been inserted into the image to designate the boundary between the media, adventitia 440 and perivascular tissues 447. In this depiction, the nerve bundles appear as hpyoechoic regions within the adventitial tissues. It will be appreciated that prior to tissue characterization, many of the structures are difficult for a user to distinguish or interpret. In one aspect, the appearance of some tissues depends on the angle of incidence of the ultrasound, such as nerve bundles and muscle fibers, such that a plurality of images may need to be analyzed to more fully characterize the tissues. FIG. 6B illustrates a Movat's pentachrome stained histology section highlighting nerve bundles 443, and muscle fibers 447 in the adventitial perivascular tissue. As explained more fully above with respect to FIGS. 4A and 4B, most of the nerve bundles are located in the perivascular tissues that form the adventitial tissues being characterized. It will be appreciated that after tissue characterization, the tissue structures of the IVUS images may be colorized on a display to better highlight these features for a user. The display may take the form of a colorized version of FIG. 6A. In an alternative form, the display may be a longitudinal cross section of the vessel, showing the adventitial tissues on either side of the vessel with color coding used to distinguish the various tissue types. In still a further form, a 3 or multi-dimensional model may be constructed utilizing the tissue characterization data to display a 3 or multi-dimensional model of the nerve bundle and or muscle fibers surrounding the vessel. It will be appreciated that in one display mode, only the nerve tissue can be displayed in a 3 or multi-dimensional model. This type of display can be particularly beneficial when combined with an ablation characterization system such that nerve ablation can be visualized in a 3 dimensional model in real-time.

The imaging apparatus 100 in the pictured embodiment is an intravascular ultrasound (IVUS) apparatus. The entire IVUS apparatus may extend through the body and include all the components associated with an IVUS module, such as a transducer(s), multiplexer(s), electrical connection(s), etc., for performing IVUS imaging. The imaging apparatus 100 of the pictured embodiment may utilize any IVUS configuration that allows at least a portion of the body to be introduced over a guidewire. For example, in some instances, the imaging apparatus utilizes an array of transducers (e.g., 32, 64, 128, or other number transducers) disposed circumferentially about the central lumen 925 of the body 920 in a fixed orientation. In other embodiments, the IVUS portion is a rotational IVUS system. In some instances, the imaging apparatus includes components similar or identical to those found in IVUS products from Volcano Corporation, such as the Eagle Eye® Gold Catheter, the Visions® PV8.2F Catheter, the Visions® PV 0.018 Catheter, the Visions® PV 0.035 Catheter and/or the Revolution® 45 MHz Catheter, and/or IVUS products available from other manufacturers. Further, in some instances the catheter 850 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,0854,109, 6,123,673, 6,165,128, 6,283,920, 6,309,339; 6,033,357, 6,457,365, 6,712,767, 6,725,081, 6,767,327, 6,776,763, 6,779,257, 6,7854,157, 6,899,682, 6,962,567, 6,976,965, 7,097,620, 7,226,417, 7,641,4854, 7,676,910, 7,711,413, and 7,736,317, each of which is hereby incorporated by reference in its entirety.

In alternate embodiments, the imaging apparatus 980 may be or include, by way of non-limiting example, any of grey-scale IVUS, forward-looking IVUS, rotational IVUS, phased array IVUS, solid state IVUS, spectroscopy, or optical coherence tomography. It is understood that, in some instances, wires associated with the imaging apparatus extend along the length of the elongated tubular body through the handle and along electrical connection to the interface such that signals from the imaging apparatus can be communicated to the controller. In some instances, the imaging apparatus communicates wirelessly with the controller and/or the processor.

The devices, systems, and methods described herein may be used to characterize tissue and provide real-time feedback as to the level of ablation during a variety of diagnostic, ablation and/or neuromodulation applications, including without limitation: carotid body ablation, cardiac ablation (including myocardial), renal neuromodulation, intravascular lesion ablation, and chronic total occlusion crossing. In each of these embodiments, the database or memory would be configured to contain pre-determined tissue imaging properties and secondary parameters associated with particular types of tissue at varying levels of ablation. The imaging apparatus utilizes this database 245 to compare and correlate the signal properties of the tissue-of-interest with the pre-determined properties to accurately characterize the tissue.

Referring now to FIG. 7, there is shown a partial cross-sectional view of a blood vessel 700 with a lesion 712 partially occluding lumen 710. The lesion 712 has disrupted the intimal layer 714 and in various locations has disrupted the medial layer 716 such that there is no distinguishable boundary between the medial layer 716 and the adventitial layer 718. Utilizing the tissue characterization techniques discussed above, the small arterioles (vasa vasorum and neo vasa vasorum) in the adventitial or medial layers may be distinguished. In one aspect, the flow of fluid within the small arterioles can be detected by changes between different scans such that a characterization technique can determine the presence, location and extent of the arterioles 720. As shown in FIG. 7, traditional tissue characterization techniques would provide information concerning the make-up and length L1 of lesion 712. Based on this information, a stent may be deployed based on the length L1 to treat the lesion and restore effective blood flow through lumen 710. Unfortunately, already distressed vessel walls on either end of the stent may continue with disease progression and form a further blockage adjacent a stent. Utilizing tissue characterization outside the intimal layer 714, the arterioles can be imaged and characterized as an indication of the extent of disease progression. Based on this additional information, it can be determined that a much greater length L2 of the vessel is responding to distress by the growth of arterioles to supply oxygen for continued cell growth.

Referring now to FIGS. 8A and 8B, there is shown a pair of angiographic images illustrating the impact of myocardial bridging on a coronary artery 810. In FIG. 8A, the coronary artery 810 is shown during the contraction of the heart with the myocardial bridging occurring between the arrows A substantially decreasing the volume of blood that can pass through the coronary artery. In FIG. 8B, the heart muscle is in a relaxed state thereby allowing substantially complete flow of blood through the coronary artery 810'. This condition is often very difficult to image utilizing standard angiography. Utilizing an imaging system 110 similar to the one disclosed with respect to FIG. 1, the coronary artery in the area of the myocardial bridging can be imaged to better determine the extent of the myocardium encroachment and determine the best approach for a therapeutic treatment. Although myocardium usually appears echolucent on gray scale images configured for imaging intimal plaques, the imaging system 110 may be configured to utilize an imaging energy or direction that is better suited to image the adventitial tissues surrounding the vessel lumen to detect myocardial bridging. Referring to FIGS. 9A and 9B, the cross-sectional image of the coronary artery 810 shows a normal intima 820 and media 822, but myocardium 830 surrounds greater than 50 percent of the circumference of the vessel and in some locations 834 has direct contact with the adventitia. In adjacent regions, the myocardium overlies the artery but is spaced from the border 826 of the adventitia 824. While the myocardium is shown as a single band of muscle, it will be appreciated that the myocardium may be composed of a number of separate fibers. Thus, utilizing adventitial tissue characterization, including the perivascular tissues, healthcare providers can better determine the location and extent of myocardial bridging about coronary vessels. As explained above, a 2 dimensional image or 3 dimensional model may be displayed illustrating the detected presence of myocardial tissue in the adventitial tissues.

Referring now to FIG. 10, there is shown a partial cross-sectional side view of a vessel 1000 with a stent 1010 placed therein. The stent 1010 is positioned in abutting relation with the vessel wall 1002. FIG. 11A shows a first axial cross-sectional view taken along line 11-11 in FIG. 10. In FIG. 11A, the image is divided by line M to represent the initial implantation orientation to the left and vessel changes after the stent has been implanted for a significant period of time on the right. With reference to the initial implantation portion, stent strut 1004 is in intimate contact with vessel wall 1002, while stent strut 1006 is spaced from the vessel wall forming a void 1008. The vessel, including the stent, can then be imaged by an imaging system such as shown in FIG. 1. In one aspect, the memory 245 includes imaging characteristics and properties associated with a variety of stents implanted within vessels. In one feature, the user is prompted to input the stent model and length, which if matching stored look-up data, allows more efficient characterization of the stent material and surrounding tissues. The characterization application 250 then compares the return ultrasound echoes taken of the vessel 1000 with the implanted stent 1010. In one aspect, the relatively bright return echoes from the stent can be subtracted from the other echoes such that tissue adjacent the struts can be more effectively imaged. For example, the characterization system may more clearly recognize the void 1008 once the bright strut returns have been removed. The characterizations conducted upon initial implantation can be stored for later use.

Referring to the right half of FIG. 11A representing the stent after indwelling for a significant time period, it can be seen that plaque 1009 has formed around stents 1004' and 1006'. An imaging system may be reinserted into the vessel having the stent 1010 and additional imaging information can be generated. In addition to characterization of the return information as set forth above, the characterization application 250 can compare characterizations performed during initial implantation to those obtained after the stent has been indwelling for an extended period. Although the intense returns off of the stent struts tend to obscure other structures, by subtracting the stent strut returns based on lookup data in the memory 245 or prior scans of the same region, other structures such as plaque 1009 can now be more effectively imaged and characterized. The difference between original characterization and the new characterization data can be displayed visually for the user.

FIG. 11B illustrates an alternative embodiment of the stent 1010' implanted within the vessel wall 1002. The stent 1010' has stent struts coated with a bioresorbable drug eluting coating. As shown on the left side of line M, when initially implanted stent struts 1012, 1014 have bioresorbable coatings 1013, 1015, respectively. Information concerning the thickness of the coatings and/or the struts themselves may be obtained from the manufacturer and stored in memory 245 or it may be obtained by scanning the stent after placement and determining the properties by characteristics techniques as discussed above. As illustrated by the right half of FIG. 11B, after the stent 1010' has been indwelling for a significant period of time the coatings with be at least partially resorbed by the body. As shown on the right side of line M', strut 1012' still has a coating 1013', although the coating has been reduced substantially in thickness. In contrast, the coating on strut 1014' has completely dissolved and is no longer present. The lack of a drug eluting coating may also be indicated where plaque 1009' has formed on the now bare metal stent struts. Consistent with the disclosure above, an imaging system may be positioned within the bioresorbable stent to image the stent after indwelling for a period of time. A characterization technique can compare the sensed bioresorable coating with the initial coating thickness to provide the user with an estimation of how much of the coating dissolved over the given period of implantation along with an estimation of how much longer the drug eluding bioresorbable coating may continue to be effective for the patient.

Referring now to FIG. 11C, there is shown a further alternative stent 1010" representing a stent formed of a bioresorbable material such that the stent struts 1020 and 1022 dissolve in the body over time. As described above the bioresorbable scaffold of stent 1010" may be imaged by an imaging device and the resulting scan and/or characterization stored for later use. As part of the characterization process, manufacturer information about the stent can be utilized to provide a better, more accurate characterization of the sensed stent and tissue information. After the stent has been indwelling for a period of time, an imaging system may be positioned within the bioresorbable stent to image the stent and surrounding tissue. A characterization technique can compare the detected bioresorbable material of struts 1020' and 1022' along with the surround tissue structures with the saved characterizations from the initial implantation. The changes in both stent strut dimension and surrounding tissue identified during the characterization process can be displayed for a user.

Referring now to FIG. 12A, there is shown a vessel 1200 with an occlusion 1212 that totally occludes side branch 1210. As discussed above and shown more fully in FIG. 7, the plaque forming the occlusion 1212 often disrupts the intima and the media, along with the media and adventitia boundary making plaque segmentation or border detection difficult. Still further, when using forward looking imaging, the angle of incidence between the emitted signals and the vessel tissue make border detection difficult. In one embodiment according to the present disclosure, an imaging device images the adventitia of a vessel to thereby assist the user in determining a safe path for crossing the occlusion. In one example, a forward looking imaging catheter 1250 is inserted into the vessel 1200. The catheter 1250 is advanced to the side branch 1210 with the imaging element 1252 energized to visual the structures in front of the catheter. In the position shown in FIG. 12A, the catheter tip is oriented along longitudinal axis L12 creating field of view FV12. As shown more fully in FIG. 12B, the field of view displays a portion of the lumen 1220, the occlusion 1212 and the adventitial tissue 1222. Utilizing the tissue characterization techniques discussed above, the system can provide a display to a user in virtually real time to show the user whether the selected path intersects adventitial tissue thereby leading to a rupture of the vessel. As shown in FIG. 12B, while the longitudinal axis L12 passes through the occlusion 1212, it also dissects adventitia 1222 such that the proposed path is a poor choice and should be avoided by the user.

Referring now to FIG. 13A, the forwarding looking imaging catheter 1250 has been repositioned in vessel 1200 such that the longitudinal axis L13 extends at a different angle with respect to side branch 1210. As shown more fully in FIG. 13B, the field of view display FV13 shows that the device is oriented along longitudinal axis L13 to extend across occlusion 1212 and remain within lumen 1220 of the side branch 1210. Tissue characterization is utilized to identify the adventitial tissue 1222 that is displayed on the borders of the field of view. In this manner, imaging and tissue characterization of the adventitial tissue can be utilized to define a path across the occlusion. While illustrated in terms of utilization of a forward looking imaging system, a similar technique can be utilized with side looking imaging devices.

Referring now to FIGS. 14A and 14B, there is shown a further forward looking image device and representative vessel image. The imaging system 1400 includes a catheter body 1402 with an ultrasonic transducer 1404 oriented to extend at an angle, for example 45 degrees, with respect to the longitudinal axis such that when the transducer is rotated around the catheter longitudinal axis a conical imaging area 1406 is created. This type of device may be used in a manner similar to the system discussed with respect to FIGS. 12A-13B. More specifically, an output image 1408 may be generated that can display the results of a tissue characterization analysis to display to the user the adventitia tissue and/or boundaries between adjacent tissue types. As explained above, when the adventitia tissue is displayed on the border of the displayed image, the area in front of the catheter may be entered to cross a chronic total occlusion.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. A method, comprising:
   inserting an intravascular imaging device into a lumen of a vessel;
   receiving, at a computing device in communication with the intravascular imaging device, imaging data representative of the vessel including surrounding adventitial tissue after therapy within the vessel, the imaging data obtained by the intravascular imaging device while positioned in the lumen of the vessel;

performing, using the computing device, tissue characterization to identify therapeutically treated tissue and one or more tissue characteristics within the adventitial tissue resulting from the therapy by comparing and matching signal properties of the imaging data to pre-determined signal properties of a plurality of tissue components including therapeutically treated tissue characteristics, wherein the therapeutically treated tissue characteristics include a plurality of ablation levels; and outputting, to a display device in communication with the computing device, an image of the vessel to a user, wherein the outputting includes displaying, within the image of the vessel, the therapeutically treated tissue and the one or more tissue characteristics within the adventitial tissue resulting from the therapy.

2. The method of claim 1, wherein the tissue characterization includes identifying nerve bundles within the adventitial tissue.

3. The method of claim 2, wherein imaging includes imaging the adventitia and the perivascular tissue surrounding an artery, and the identifying includes identifying nerve bundles within the perivascular tissue.

4. The method of claim 1, wherein the displaying includes displaying an axial cross section of the vessel showing tissue characterization within the adventitial tissue.

5. The method of claim 1, wherein displaying includes displaying a longitudinal cross sectional view of the vessel showing tissue characterization within the adventitial tissue.

6. The method of claim 1, further including identifying areas of adventitial tissue impacted by the therapy.

7. The method of claim 6, wherein said areas include nerve bundles.

8. The method of claim 1, further including performing a first imaging of the vessel and first tissue characterization of the adventitial tissue of the vessel, conducting a therapy on the vessel, performing a second imaging of the vessel and second tissue characterization of the adventitial tissue of the vessel, comparing the first and second tissue characterizations and displaying the differences to the user.

9. The method of claim 1, wherein the tissue characterization includes identifying vasa vasorum in the adventitial tissue of the vessel.

10. The method of claim 9, wherein the displaying includes displaying an axial cross section of the vessel showing the vasa vasorum within the adventitial tissue.

11. The method of claim 9, wherein displaying includes displaying a longitudinal cross sectional view of the vessel showing the vasa vasorum within the adventitial tissue.

12. The method of claim 9, further including displaying tissue characteristic information for other portions of the vessel.

13. The method of claim 12, wherein the other tissue characteristics include plaque within the artery.

14. The method of claim 9, further including providing information to the user on the length of enhanced vasa vasorum growth along the length of the blood vessel.

15. The method of claim 14, further including determining a stent length at least in part of the detected vasa vasorum growth adjacent a lesion.

16. The method of claim 9, further including imaging a vessel including a stent, characterizing the adventitial tissue adjacent the stent to determine vasa vasorum growth, and evaluating vessel health adjacent the stent based on the vasa vasorum growth.

17. The method of claim 1, wherein the tissue characterization includes identifying muscle tissue within the adventitial tissue of the vessel.

18. The method of claim 17, wherein the displaying includes displaying an axial cross section of the vessel showing the muscle tissue within the adventitial tissue.

19. The method of claim 17, wherein the displaying includes displaying a longitudinal cross sectional view of the vessel showing the muscle tissue within the adventitial tissue.

20. The method of claim 17, wherein the tissue characterization includes identifying a border between the adventitial tissue and overlying muscle tissue.

21. The method of claim 1, further including imaging a stent disposed in the vessel and comparing the sensed image data to a data base of know stent patterns.

22. The method of claim 21, further including subtracting a stent image from the vessel image to permit better display of tissue characterization.

23. The method of claim 21, further including comparing stent image return echoes to a data base of known stent patterns and displaying detected deviations between the sensed stent image and the data base stent patterns.

24. The method of claim 23, wherein the stent includes one or more bioresorbable materials and displaying detected deviations includes displaying changes based in the resorbable stent material.

25. The method of claim 21, further including evaluating the stent for the development of plaques on the stent and displaying the detected plaques to a user.

26. The method of claim 21, further including evaluating the placement of stent struts against the interior of the vessel.

27. The method of claim 1, wherein the pre-determined signal properties includes at least two or more of: a first signal property representative of minimally ablated tissue, a second signal property representative of moderately ablated tissue, a third signal property representative of majorly ablated tissue, or a fourth signal property representative of completely ablated tissue.

28. The method of claim 1, wherein the outputting further includes displaying a graphical representation of the tissue characterization including the therapeutically treated tissue characteristics.

29. A system for adventitial tissue characterization, the system including:

a data base of known signal properties representative of tissue components including therapeutically treated tissue characteristics within a vessel including an adventitia, wherein the therapeutically treated tissue characteristics include a plurality of ablation levels;

an intravascular imaging device sized and shaped to be positioned in a lumen of a vessel, the intravascular imaging device including a sensor for collecting imaging data from the vessel including the adventitia; and a processor in communication with the data base and the intravascular imaging device, the processor configured to:

compare the imaging data obtained while the intravascular imaging device is positioned in the lumen of the vessel after therapy within the vessel to the data base of known signal properties representative of tissue components including therapeutically treated tissue characteristics within the vessel including the adventitia;

determine therapeutically treated tissue and tissue characteristics within the adventitia resulting from the therapy based on the comparison, wherein the therapeutically treated tissue is determined based on one of the therapeutically treated tissue characteristics;

evaluate health of the vessel based on the therapeutically treated tissue and the tissue characteristics within the adventitia resulting from the therapy; and output, to a display device in communication with the processor, an image of the vessel including the therapeutically treated tissue and the tissue characteristics within the adventitia resulting from the therapy.

30. The system of claim 29, wherein the processor is configured to determine the therapeutically treated tissue by matching a signal property of the imaging data with one of the known signal properties of the tissue components that include one of the therapeutically treated tissue characteristics.

31. The system of claim 30, wherein the known signal properties includes at least two or more of: a first signal property representative of minimally ablated tissue, a second signal property representative of moderately ablated tissue, a third signal property representative of majorly ablated tissue, or a fourth signal property representative of completely ablated tissue.

32. A method for utilizing tissue characterization in image guided therapy, comprising:

positioning an intravascular imaging device within the lumen of a vessel; obtaining first imaging data of the vessel including adventitial tissue surrounding at least a portion of the lumen;

performing a first tissue characterization on the first imaging data to identify tissue characteristics within the adventitial tissue;

displaying a first image of the vessel including the tissue characteristics within the adventitial tissue to a user;

obtaining second imaging data of the vessel after therapy is performed on the at least a portion of the lumen, the second imaging data including therapeutically treated tissue and the adventitial tissue surrounding the at least a portion of the lumen;

performing a second tissue characterization on the second imaging data to identify the therapeutically treated tissue and changes in the tissue characteristics within the adventitial tissue resulting from the therapy by comparing and matching signal properties of the second imaging data to pre-determined signal properties of a plurality of tissue components including therapeutically treated tissue characteristics, wherein the therapeutically treated tissue is identified based on one of the therapeutically treated tissue characteristics, wherein the therapeutically treated tissue characteristics include a plurality of ablation levels; and displaying the second image of the vessel including the therapeutically treated tissue and the changes in the tissue characteristics within the adventitial tissue resulting from the therapy.

33. The method of claim 32, further including:

positioning a therapy device within the lumen of the vessel;

defining a longitudinal direction of the therapy device; and alerting to the user to the presence of adventitial tissue in the longitudinal direction of the therapy device.

34. The method of claim 32, further comprising changing a longitudinal direction of the device in response to the displaying the first image of the vessel including the tissue characteristics within the adventitial tissue.

35. The method of claim 34, wherein the therapy device is an ablation device and the changing includes changing a longitudinal position or a radial position of the ablation device within the vessel in response to the adventitial tissue characteristics.

* * * * *